United States Patent [19]

Lo et al.

[11] Patent Number: 4,954,960
[45] Date of Patent: Sep. 4, 1990

[54] LINEAR POWER CONTROL FOR ULTRASONIC PROBE WITH TUNED REACTANCE

[75] Inventors: Ying-Ching Lo, Fremont; Samuel Zambre, Palo Alto; Tolentino Escorcio, San Leandro, all of Calif.

[73] Assignee: Alcon Laboratories, Fort Worth, Tex.

[21] Appl. No.: 35,128

[22] Filed: Apr. 6, 1987

Related U.S. Application Data

[63] Continuation-in-part of Ser. No. 928,235, Nov. 7, 1986.

[51] Int. Cl.$^5$ .................... G01H 13/00; G01H 15/00
[52] U.S. Cl. .................... 364/484; 364/482; 364/571.01; 323/208; 323/205; 324/654; 318/729; 331/181
[58] Field of Search ............... 364/481, 482, 483, 492, 364/484, 571.01; 323/207, 208, 209, 210, 206, 205; 318/116, 729; 324/56, 57 R, 59, 60 R; 331/154, 155, 158, 181

[56] References Cited

U.S. PATENT DOCUMENTS

| | | | |
|---|---|---|---|
| 3,432,691 | 3/1969 | Shoh | 310/316 |
| 3,936,727 | 2/1976 | Kelly, Jr. et al. | 323/210 |
| 3,963,978 | 6/1976 | Kelly, Jr. et al. | 323/210 |
| 3,968,432 | 7/1976 | Kelly, Jr. | 324/107 |
| 3,992,661 | 11/1976 | Kelly, Jr. | 323/210 |
| 4,013,937 | 3/1977 | Pelly et al. | 323/207 |
| 4,028,614 | 6/1977 | Kelly, Jr. | 323/210 |
| 4,525,790 | 6/1985 | Nakamura | 364/484 |
| 4,551,690 | 11/1985 | Quist | 331/362 |
| 4,605,890 | 8/1986 | Nakanura | 304/483 |
| 4,623,838 | 11/1986 | Nakamura | 364/483 |
| 4,626,728 | 12/1986 | Flachenecker et al. | 318/116 |

FOREIGN PATENT DOCUMENTS 1130442 5/1969 United Kingdom.

Primary Examiner—Parshotam B. Lall
Assistant Examiner—V. N. Trans
Attorney, Agent, or Firm—Ronald C. Fish

[57] ABSTRACT

A driver system for an ultrasonic probe using a tunable inductor in series with the piezoelectric crystal excitation transducer in the probe. The bias current through this flux modulation coil is controlled by the system such that the inductance of the tunable inductor cancels out the capacitive reactance of the load impedance presented by the probe when the probe is being driven by a driving signal which matches the mechanical resonance frequency of the probe. The resulting overall load impedance is substantially purely resistive. The system also adjusts the frequency of the driving signal to track changing mechanical resonance conditions for the probe at different power levels. This method of operation insures substantially maximum power transfer efficiency and substantially linear power control over a range of power dissipation levels. The system determines the mechanical resonance frequency by sweeping the drive frequency and monitoring the drive current to determine the frequency at which the drive current is a maximum.

7 Claims, 22 Drawing Sheets

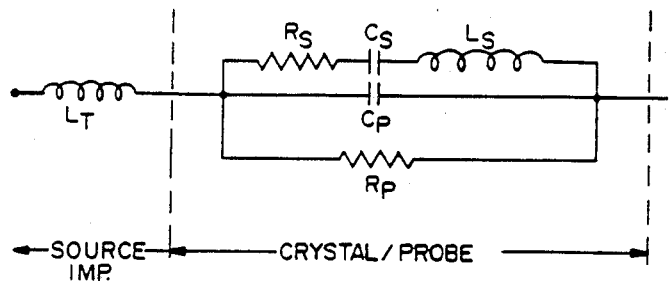
FIG. 2
(A) $\omega_S = \dfrac{1}{\sqrt{L_S C_S}}$  (B) $L_T = \dfrac{(R_S \| R_P)^2 C_P}{1 + \omega_S^2 C_P^2 (R_S \| R_P)^2}$  AT $\omega_S$
FIG. 3
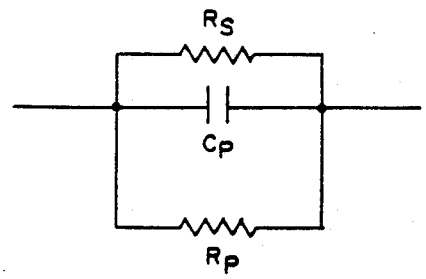
FIG. 4

FIG. II

FIXED POWER
FIXED FREQUENCY
WITH TUNING INDUCTOR

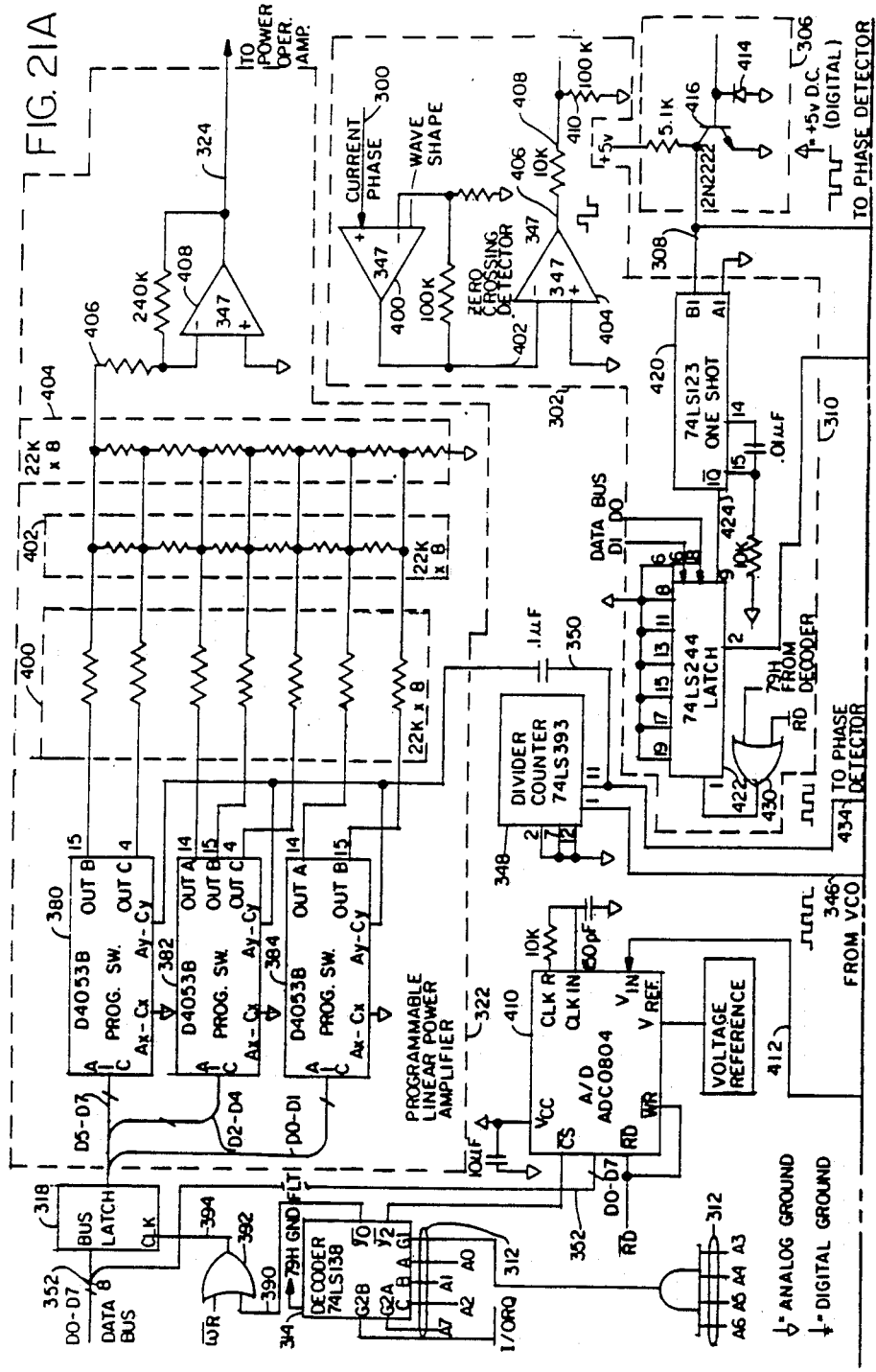

SWEEPER ROUTINE
(FREQUENCY)

LINEAR POWER CONTROL FOR ULTRASONIC PROBE WITH TUNED REACTANCE

BACKGROUND OF THE INVENTION

This is a continuation in part application of a U.S. patent application by Lo et al. entitled "Linear Power Control for Ultrasonic Probe With Tuned Reactance", ser. No. 928,235, filed Nov. 7, 1986 which is currently co-pending.

The invention relates to the field of phacoemulsification probe driving apparatus, and, more particularly, to the field of tuned reactance process for phacoemulsification.

It has long been known that, in delivery of electric power to inductive loads or capacitive loads. maximum efficiency and maximum delivery of said power occurs when the phase angle between the voltage across the load and the current through the load is substantially zero. The phase angle of a system is related to the power factor. Those skilled in the art appreciate that the impedance of any network which includes inductive or capacitive elements in addition to resistive elements is the vector sum of the real component, i.e., the resistive elements, and the imaginary component caused by the presence of the inductive and capacitive elements. If the reactive component is zero, then the impedance of a system is purely resistive. and the resultant vector is coincident with the real axis. In such a circumstance, the phase angle is zero. Power factor is a measure of the relative magnitudes of the reactive and real components in a load impedance. It is related to the relative magnitude of these two vector components.

Power factor is also a measure of the efficiency of a system in delivering power to a load. Since only resistive components can actually dissipate power, the presence of an inductive or capacitive reactance component in a load impedance will decrease the efficiency of power delivery of the system, since it causes increased power dissipation in the source resistance of the power supply. The reason for this is well understood by those skilled in the art and will not be detailed here. As a consequence of the foregoing reality, it has long been known by utility companies and other practitioners of the power delivery art that to maximize the efficiency of power delivery to a load, it is useful to tune out the reactive component of the load impedance by placing it in series or parallel with an equal and opposite sign reactive component in a tuning circuit so that the resultant load impedance is purely resistive. In such a circumstance the source impedance is said to be the matched conjugate of the load impedance, and the power delivered to the load is maximized.

Power delivered to a load is given by the following expression:

$$\text{Power} = VI \cos\Theta \quad (1)$$

where V is the voltage drop across the load impedance, and I is the series current flowing through the load impedance, and cosine theta$\Theta$ is the power factor of the circuit. The power factor is said to be "leading" if the current leads the voltage, and "lagging" if the current lags the voltage.

Ultrasonic probes have traditionally been used for phacoemulsification for rupturing of cataracts in the eye coupled with aspiration of the pieces of tissue disrupted by the probe. There have been developed two classes of probes, one of which is excited by piezoelectric crystals. Such piezoelectric probes traditionally have been rods of metal, such as titanium, having piezoelectric crystals affixed therein to act as excitation sources to cause the rods to vibrate. The piezoelectric crystals are driven with electrical alternating current driving signals having high frequencies, such as 40,000 Hz. The length of the probe is such that it is a multiple of one-half the wavelength of the driving signal. Vibration of the piezoelectric crystal under the influence of the driving signal causes the rod to vibrate at its mechanical resonant frequency.

The piezoelectric crystals which are used as excitation sources in such probes, when coupled with the mass of the probe rod, can be modeled as an equivalent electrical circuit having inductive, capacitive, and resistive components. There is a capacitive component representing the elasticity of the metal of the rod and and inductive component representing the mass of the probe. There is also a resistive component representing resistance to motion of the tip of the rod as it hits loads such as tissue or fluids in the eye which tend to dampen the vibration of the tip of the probe. The piezoelectric crystal itself contributes a resistive component which is related to the amount of leakage of current between the terminals of the crystal. The crystal also has a capacitive component which represents the intrinsic electrical characteristics of piezoelectric crystals, i.e., the thickness and the dielectric constant and the area.

As the temperature changes, and as load on the probe changes, the various resistive and reactive components in the equivalent circuit of the probe change values. These changes in the component values change the mechanical resonant frequency of the probe. Unless the driving frequency is changed to correspond with the changed resonant frequencies, maximum power-transfer efficiency will not be achieved.

Further, those skilled in the art understand that maximum power transfer between a source and a load occurs when the impedances of the source and the load are matched so that the load appears to be purely resistive. Therefore, in the case of an ultrasonic probe if the probe load impedance at the resonance frequency has a capacitive reactive component, the source impedance should have an inductive reactive component of equal magnitude to maximize power transfer between the source and the load. Because of the changing magnitudes of the resistive and reactive components of the combined mechanical and electrical system of a phacoemulsification probe, as the power level changes and as the temperature and load conditions of the probe change it is difficult, if not impossible with a fixed inductor, to match the source impedance to the load impedance to cancel out the probe's reactive component over a broad range of power levels and frequency variations. An advantage of such a matched, tuned system is that low voltage components may be used since the impedance seen by the source voltage generator is minimized (looking into a two-port network including the tuning inductor).

Accordingly, there has arisen a need for a phacoemulsification probe driver which can be tuned such that the reactive component of the load is cancelled as conditions such as power level, temperature, and loading change. Further, there has arisen a need for a probe driver circuit which can alter the driving frequency to match the changed mechanical resonant frequency as power level, temperature, and loading conditions change or as new probes are attached to the system. Further, a need has arisen for a phacoemulsification probe driver with proportional power control such that the user may set a desired power level and that level of power will be transmitted to the probe.

SUMMARY OF THE INVENTION

According to the teachings of the invention, there is disclosed herein a method and apparatus for providing substantially proportional power control for a phacoemulsification probe. There is also disclosed an apparatus and method for providing constant tuning of the source impedance reactive component for the driver of a phacoemulsification probe driver to maximize the efficiency of power transfer from the driver to the probe by cancelling the reactive component of the equivalent circuit of the phacoemulsification probe. There is also disclosed an apparatus and method for tuning the phacoemulsification probe driver frequency to substantially match the changing mechanical resonant frequency of the probe as power level, temperature, and loading conditions change or as different probes are attached to the system.

In one embodiment, the linear power control apparatus includes a microprocessor which is coupled through a serial interface to a foot pedal control manipulated by the user to set the desired level of power. The microprocessor is also coupled to a maximum power level control on the front panel, which is also manipulated by the user to establish the 100% power level. The microprocessor reads the foot pedal position and the position of the maximum power level control on the front panel and scales the signal from the foot pedal to determine the desired power level as a percentage of the maximum level set by the user at the front panel. The microprocessor then generates a digital gain number and sends it to a programmable gain linear power amplifier. This amplifier is also coupled to a driving signal frequency generator in the form of a voltage controlled oscillator. The programmable linear power amplifier amplifies the driving signal by the gain level established by the digital input from the microprocessor. This programmable amplifier can be combined with the voltage controlled oscillator in some embodiments since commercially available VCO's with linear gain exist. The output of the linear programmable amplifier is then amplified by another power amplifier operating in class AB. The output of this amplifier is applied to a voltage step-up transformer which has its secondary coupled through a tuning inductor to the piezoelectric crystal or crystals which excite the phacoemulsification probe.

The tuning inductor is the means by which the source impedance of the probe driver circuitry may be adjusted so that the driver circuitry source impedance is maintained so as to cancel the reactive component of the load impedance presented by the crystal and the mechanical system of the probe. The tuning inductor, in the preferred embodiment, is comprised of a ferromagnetic core with three arms extending therefrom. Two of these arms have the AC driving signal coils wrapped around them. The AC driving signal then sets up a magnetic flux through the core. Part of which passes through the third arm. The third arm has wrapped thereabout a magnetic flux modulating coil which has a DC current flowing therein at an amplitude controlled by the microprocessor. The purpose of the tuning inductor is to allow the microprocessor to control the amount of inductance which is in series with the load impedance such that the source impedance may be tuned to cancel the reactive component of the load impedance for all load, temperature, and power level conditions. Any tunable inductor which can be used to cancel the capacitive reactance of the load will suffice for purposes of practicing the invention.

In order to control the reactive component of the source impedance, the microprocessor needs to sense the power factor or phase angle between the phasor representing the current waveform for current flowing through the piezoelectric crystal load and the waveform representing the driving voltage across the piezoelectric crystal load. A phase detector is used for this purpose. It has one input which samples the voltage waveform for the driving voltage across the crystal and it has another input which samples the current waveform for the driving current through the crystal. This current waveform sampling is taken from a tap on the primary side of the voltage step-up transformer. This transformer has incorporated in the return side thereof a current sensing resistor in one embodiment. The voltage drop across this resistor is proportional to and in phase with current flowing through the primary of the step up transformer. It is the phase angle between the current flowing in the primary and the voltage across the primary which is tuned by the system to be zero or some other user defined, acceptable phase angle so as to cancel the reactive component of the load. Any other means of sensing the phase of the load current will also suffice for purposes of practicing the invention. For example, a current probe or current sense transformer could be used.

The phase detector generates two pulse-Width modulated digital signals which represent the magnitude of the phase and its sign. These pulse-width modulated signals are summed and integrated to generate an analog signal representing the magnitude of the phase angle error. This analog signal is converted by an A/D converter to a digital number representing the phase angle error. Any phase angle other than zero represents an out-of-tune condition where the reactance of the probe impedance is not cancelled. When the phase angle is nonzero (or whatever acceptable phase angle the user sets in some embodiments), the microprocessor senses this fact and alters the DC current flowing through the magnetic flux modulating coil in the tuning inductor. This alters the amount of magnetic flux in the core passing through the AC driving coils of the tuning inductor, thereby altering the inductance thereof. This process is continued with small changes to the drive current of the DC. coil until the reactive component of the probe impedance is cancelled and the source drive impedance is a matched conjugate of the probe impedance.

The preferred embodiment of the invention is functionally equivalent to the embodiment described above except that certain details are changed. The preferred embodiment does not use a current sense resistor. Instead, a current sense transformer is used. Further, two comparators are used between the inputs of the phase detector and the two phase signal inputs. Each comparator compares the driving signal amplitudes to zero and generates a series of state changes at the outputs. The time difference between these state changes is used by the phase detector to determine the phase angle. These state changes are also monitored by the microprocessor to determine whether a ground fault exists indicating that there is something wrong with the probe driving circuitry. The preferred embodiment also uses one of the legs of the driving transformer core as the A.C. driving coil support and uses the other two legs for supports for two halves of the D.C. tuning coil. The preferred embodiment also does not use a linear programmable amplifier. Instead, it uses a digital to analog converter and an amplitude modulation control input on the voltage controlled oscillator. In this way, the user's power demands transmitted to the microprocessor from the foot pedal are converted by the microprocessor into a digital desired power number. These numbers are converted to analog signals levels by the digital to analog converter and coupled to the amplitude modulation control input of the voltage controlled oscillator to modulate the amplitude of the VCO output in accordance with the desired power.

The reason the voltage controlled oscillator is used is to allow the driving frequency to be altered for changing conditions and changing probes so that the driving frequency substantially matches the mechanical resonance frequency of the probe. The reason the tuning inductor is needed in the probe driving circuit is as follows. The piezoelectric crystal/mechanical system of the probe at resonance has a load impedance which has a capacitive reactance component. The inductance of the tuninq inductor, which is in series with the load impedance, is altered by the microprocessor to be equal to and opposite in character to the capacitive reactance represented by the probe. When the driving frequency matches the mechanical frequency of the probe and when the inductive reactance of the source impedance matches the capacitive reactance of the probe, the phase angle will be zero and maximum power transfer efficiency will have been achieved for the given ratios of the real components of the source and load impedances. The microprocessor alters the current flowing through the magnetic flux modulating coil, i.e., the D.C. coil, to substantially tune away the phase angle. This is done in one embodiment by generating a digital number or series of digital numbers (in incremental change embodiments) representing the amount of change desired and sending this number or numbers to a D/A converter. This converter converts the digital number(s) to an analog current which is then driven through a current driver through the D.C. magnetic flux modulating coil.

The source impedance tuning aspects of the invention are utilized for the linear power control apparatus also in some embodiments. This source impedance tuning apparatus is also useful even in systems wherein the power level is fixed. That is, the microprocessor constantly monitors the phase angle, and when changes in temperature or loading conditions cause alteration of the load impedance, a phase angle will arise. This phase angle is sensed by the microprocessor, which then alters the level of current flowing through the magnetic flux modulating coil and the tuning inductor to reduce the phase angle toward zero or the value set by the user. In this way the source impedance is maintained continuously so as to cancel the reactive component of the load at the mechanical resonance frequency, thereby insuring maximum power transfer efficiency at all times.

In both the linear power control and the source impedance tuning apparatus, the CPU uses one or more look-up tables for storing data describing the necessary flux modulating coil bias current for particular conditions of power level and temperature in some embodiments. In some embodiments, the temperature of the probe may be assumed by keeping track of the amount of power transmitted to the probe and the amount of time during which this power dissipation level is maintained in the probe. In some embodiments power level, elapsed time, or phase angle may be the criteria upon which tuning of the tuning inductor is based. In other embodiments, a temperature feedback signal may be present to provide positive indication of the probe temperature to the microprocessor. Each look-up table has data for the proper bias level to use for each possible condition of temperature. Power level, phase angle, elapsed time, or some combination of these data. These items of data are used to generate an address to access the proper bias level from the look-up table. The data accessed at each address represents the experimentally determined amount of current that should be driven through the magnetic flux modulating coil for the then existing conditions to have the source impedance of the driver tuned to cancel the reactive component of the load impedance for the probe at its mechanical resonance frequency. The microprocessor then takes the data emerging from the look-up table and sends it to the D/A converter for conversion into the proper level of bias for the magnetic flux modulating coil. In some embodiments, this first level approximation of a tuned condition will be adequate. In other embodiments, the first level approximation of a tuned condition will then be further fine tuned by actual measurement of the phase angle and further adjustment of the bias level for the magnetic flux modulating coil to cause the phase angle to reach zero or the user-defined acceptable value. The manner in which the phase angle is adjusted and the bias level of the magnetic flux modulating coil is changed is described above.

In the preferred embodiment, look up tables are nor used. Instead, a sweeper software routine sweeps the driving frequency through a range of frequencies known to include all possible mechanical resonant frequencies of commercially useable phacoemulsification probes. During this sweep, the probe drive current is monitored and compared to the highest probe driver current to that point in time. If the current frequency of the driving signal results in a probe drive current which is greater than the current highest probe driver current, the current probe driver current is replaced with the new highest probe driver current value. This process is continued until the entire range of frequencies has been surveyed. The frequency corresponding to the highest probe driver current is then set into the VCO by sending a signal to the frequency modulation input of the VCO causing it to generate a probe driving signal having the corresponding frequency. After the proper driving frequency is determined, a software routine to tune away the phase angle as much as possible is performed. This routine determines the phase angle difference between a constant reference phase angle representing the desired phase angle difference and the actual phase angle. The difference is then divided by two and used to adjust the D.C. coil bias drive. This process of successive approximation is then continued until the phase angle difference falls within an acceptable range.

Tuning the drive frequency of the probe driver to match the resonant frequency of the probe as conditions change is an important aspect of the teachings of the invention. When the ambient temperature changes or when extended use and power dissipation in the probe occurs, the temperature of the probe can change unless some mechanism is in place to stabilize the probe temperature. When the temperature of the probe changes, the magnitude of the various reactive components in the equivalent circuit representing the piezoelectric crystal and mechanical system change also. This has the effect of changing the resonant frequency of the probe system. The changes in the magnitudes of the reactive components are reflected in a changed phase angle or power factor also because of the fact that the magnitude of the reactance component of the overall impedance changes, thereby changing the angle of the resultant impedance vector with the real component. Further, as the probe encounters liquids in the eye or tissue, the mechanical loading on the probe tip changes, and this changes the value of the resistive or real component in the impedance load vector. These changes in the real component result in a changed phase angle. This is because load changes alter the vector sum and, therefore, alter the angle of the resultant impedance vector with the real component. Changes in mechanical loading can also change the resonance frequency. These changes in the resonant frequency of the probe system will result in less efficient power transfer unless the frequency of the driving waveform is altered to match the mechanical resonant frequency of the probe system. In some embodiments, the frequency of the driving waveform is altered by the microprocessor by use of one or more look-up tables containing experimentally determined data as to the resonant frequency at any particular probe temperature, phase angle, etc. In some embodiments, the microprocessor either senses the probe temperature using a temperature sensor or assumes the probe temperature, given a measured amount of power dissipation in the probe for a measured amount of time. From this real or assumed temperature data (the technique also works for power level, phase angle, or both), an address into the look-up table is derived by the microprocessor, and the data at that location is accessed. This data is then used to generate a digital frequency control word. This frequency control word is then converted to an analog signal via a D/A converter and applied to the control input of a voltage-controlled oscillator to alter the driving signal frequency to match the new mechanical resonant frequency. In the preferred embodiment, the driving frequency is changed by trial and error as described above.

The methods of linear power control, impedance matching over wide ranges of conditions, and source frequency tuning to match the resonant frequency according to the teachings of the invention may be understood from the above description of the functions of the apparatus that implements these processes.

The teachings of the invention can be better understood by reference to the following drawings.

BRIEF DESCRIPTION OF THE DRAWINGS

FIGS. 3A and 3B are two expressions of the mathematical relationships needed to explain the functioning of the system.

FIG. 4 is the simplified equivalent circuit of the probe at the mechanical resonant frequency.

FIGS. 21A and 21B together comprise a more detailed schematic diagram of the analog embodiment of FIG. 20.

DETAILED DESCRIPTION OF THE PREFERRED EMBODIMENT

Figure 1:
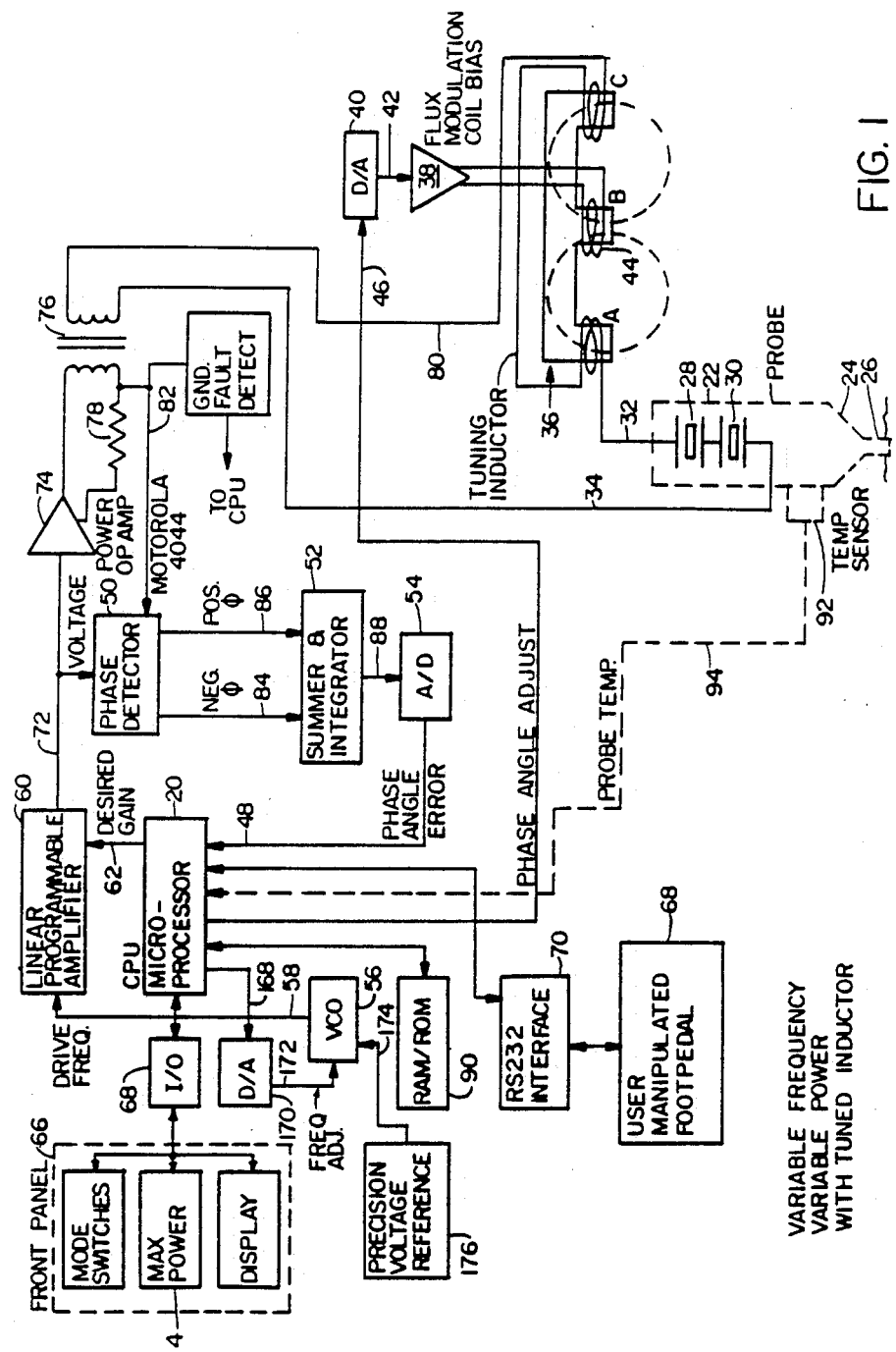
FIG. 1 is a block diagram of one embodiment of the invention which implements all teachings of the invention.

Referring to FIG. 1, there is shown a block diagram of one embodiment of the invention which implements all three aspects of the teachings of the invention. A microprocessor 20 is at the heart of the system. In one embodiment, the microprocessor 20 is part of an off-the-shelf Micro/Sys B8010 CPU card. The microprocessor 20 controls all the functions which the system performs. According to the teachings of the invention, three separate and independent function are performed, all of which can be used independently of the other functions and all of which have utility in phacoemulsification probe driver systems. The best performance, however, results from use of all three aspects of the invention in combination. The purpose and function of the various components of the system will be explained in the course of explaining each function that the system performs so that the cooperation of each individual element with the other elements in order to accomplish the function will be clear.

It is useful in phacoemulsification probe driver systems to have a substantially linear control over the amount of power dissipated in the probe. In FIG. 1, the probe 22 is a metal rod having a conical mechanical amplifier section 24 and a projecting nosepiece 26 in the form of a small diameter tube on the mechanical amplifier 24. Embedded in or otherwise mechanically attached to the metal of the probe 22 are a pair of piezoelectric crystals, 28 and 30. The purpose of the crystals 28 and 30 is to excite the metal of the probe 22 to vibrate at its mechanical resonance frequency as the crystals vibrate in response to electrical driving signals on the lines 32 and 34. Together the piezoelectric crystals 28 and 30 and the mechanical system of the probe 22 can be modeled by the equivalent circuit shown in FIG. 2. These two resistive components $R_p$ and $R_s$ represent, respectively, the leakage between lines 32 and 34 of the crystals 28 and 30 and the resistance of the mechanical load, e.g., cataract or water or other tissue, touching the tip of the projecting nosepiece 26 to movement of the projecting nosepiece 26. The value of $R_s$ changes drastically when the nosepiece 26 comes into contact with liquid such as water or other fluids in the eye versus free vibration in air. Computer simulations of the crystal/mechanical system show that $R_s$ can increase drastically with changing conditions.

As power is dissipated in the crystals, the temperature of the probe 22 can increase if sufficient mounts of power are dissipated over time. Normally the probe 22 has a fluid passageway through the nosepiece 26 to which a vacuum is applied such that tissue and eye fluids which the nosepiece comes into contact with may be aspirated through the nosepiece and into a collection cassette. This causes some cooling of the probe, so the temperature rise of the probe depends upon the thermal equilibrium between heat flowing into the probe by virtue of power dissipation in the crystal versus heat being taken out of the probe by virtue of cooler fluids being aspirated through the fluid channel (not shown) in the nosepiece 26.

As can be seen from the equivalent circuit for the crystal/mechanical probe system, the series network of capacitance and inductance representing the mechanical aspects of the probe will have a mechanical resonant frequency. Generally speaking, when the crystals 28 and 30 are driven with a frequency so as to vibrate at the mechanical resonant frequency, the series capacitance and inductance representing the mechanical aspects of the system will cancel each other out and disappear from the equivalent circuit representing the overall probe load impedance. This leaves an equivalent circuit which is dominated by the capacitance of the piezoelectric crystals as shown by FIG. 4. Thus, the load impedance has a capacitive reactance component. In order to get maximum efficiency of power transfer, this capacitive component of the load impedance must be canceled out by an equal and opposite inductive impedance in series with it. This is accomplished by use of a tuning inductor 36 having an inductance $L_T$. The tuning inductance consists of a ferromagnetic core having three legs labeled A, B, and C. Legs A and C have wound thereabout A.C. driving signal coils which are connected in series. The purpose of these coils is to provide an inductance in series with the load impedance of the probe to help cancel the capacitive reactance of the load impedance at the mechanical resonant frequency. To that end, the A.C. driving signal coils, which will hereafter be referred to as coils A and C, establish paths of magnetic flux which pass through the ferromagnetic material of legs A and C, out into the air and then back into the core through the leg B.

The leg B has wound thereabout a D.C. flux modulation coil. When D.C. is passed through this coil, the amount of magnetic flux in the ferromagnetic coil is altered. When the amount of flux in the core is altered, the inductance of the inductor changes. Thus, by controlling the magnitude of current flowing through the coil 44 wrapped around leg B (hereafter referred to as the flux modulation coil) the inductance of the tuning inductor may be changed.

The flux modulation coil 44 is coupled to the output of a voltage-to-current amplifier 38. This amplifier receives a voltage input signal from a D/A converter 40. The purpose of the voltage-to-current amplifier 38 is to convert the voltage on the line 42 from the D/A converter to a corresponding magnitude of D.C. bias current flowing through the flux modulation coil 44.

The D/A converter 40 receives as its input a phase angle adjust digital word on the bus 46 from the microprocessor. This phase angle adjust word is generated by the microprocessor 20 in response to several input data items. One of these data items is the phase angle error word on the bus 48. This phase angle error data represents the phase angle between the phasor representing the driving voltage waveform applied across the crystal load and the phasor representing the current waveform for load current flowing through the crystal. This phase angle error information is developed in part by a phase detector 50. The output of the phase detector is coupled to a summer and integrator 52, which has its output in turn coupled to an A/D converter 54.

Figure 18:
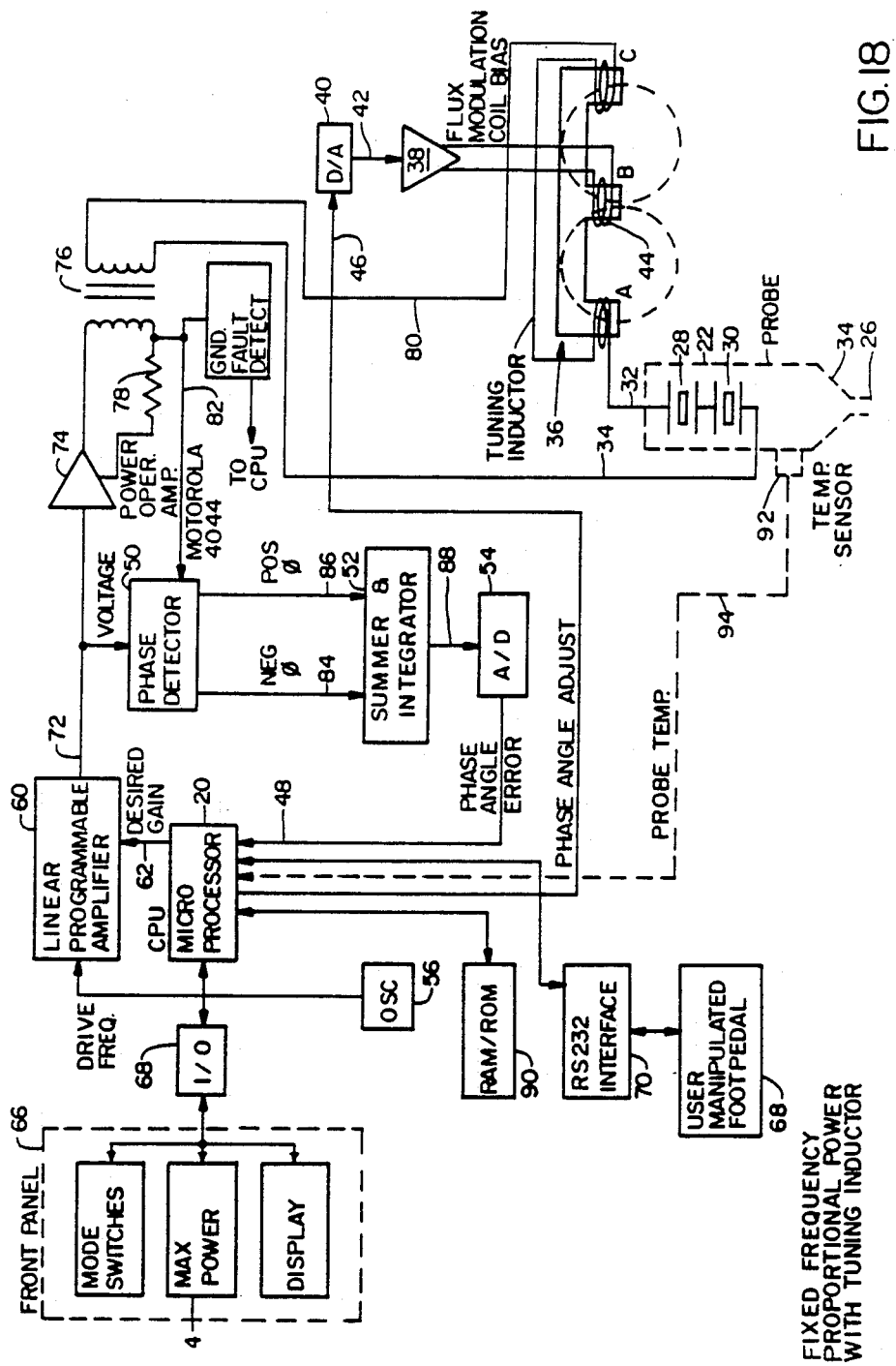
FIG. 18 is representative of a class of fixed frequency, proportional power embodiments with a tuned driving inductance to minimize the phase angle.
Figure 19:
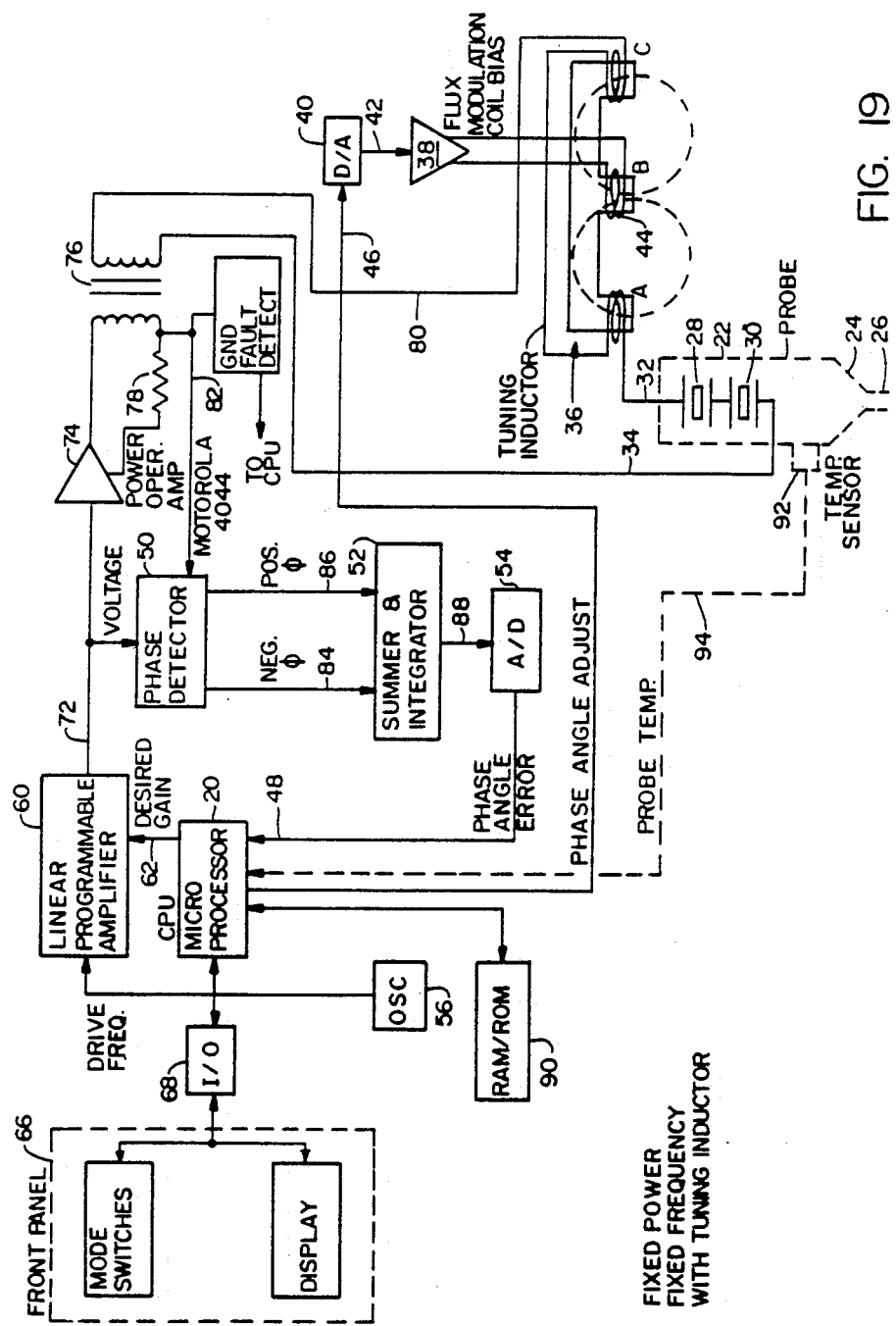
FIG. 19 is representative of a class of fixed power, fixed frequency tuned inductance embodiments.

To understand how the phase angle error adjust signal is generated on bus 48, the rest of the driving circuitry will be explained as a preliminary matter. The function of the driving circuitry is to drive the crystals 28 and 30 with an A.C. driving waveform which causes the crystals to vibrate at the mechanical resonance frequency of the probe 22. Obviously, the first step in this process is to generate a driving signal having a frequency which is equal to the mechanical resonance frequency of the probe 22. This is done, in one embodiment, by a voltage control oscillator 6. However, in some embodiments, the voltage control oscillator 56 could be a fixed frequency oscillator set at the mechanical resonant frequency for the probe for a temperature at which the probe operates most of the time. Such an embodiment is illustrated in FIGS. 18 and 19, where the FIG. 18 embodiment has proportional power control and the FIG. 19 embodiment has a fixed power level. As will be seen from discussions below, this is not an optimum situation but is acceptable under some circumstances.

The output of the oscillator on line 58 in FIG. 1 is applied to the input of a linear programmable amplifier 60. The purpose of this amplifier is to amplify the signal on the bus 58 by a gain value established by a signal on a bus 62. In one embodiment utilizing proportional power control, the data bits on the bus 62 represent the desired gain as set by the user.

In one embodiment, the user establishes the desired gain level by manipulation of two controls. The first control is the maximum power control 64 on the front panel 66. With the control 64, the user establishes the maximum power level desired. The microprocessor 20 reads this maximum power level through an I/O circuit 68 of conventional design. In one embodiment, the I/O circuit 68 is an SB8466 board manufactured by Micro/Sys of Glendale, Calif. Any conventional method and apparatus for performing the I/O transactions between the microprocessor and the front panel 66 will suffice for purposes of the invention.

The other user-operable control with which the desired power level is set is a foot pedal 68. This control allows the user to establish the desired power level as a percentage of the maximum power set by the control 64 by depressing a pedal with his foot. The depression of the foot pedal operates a transducer which may be read by the microprocessor 20 through an RS232 interface circuit 70 of conventional design. In one embodiment, the foot pedal is actually attached to a surgical instrument called the MVS-XIV or MVS-XX manufactured by Alcon Surgical, MID Labs, San Leandro, California. The MVS-XIV reads the foot pedal position and sends that information to the microprocessor 20 via the RS232 interface connecting the driver system of FIG. 1 to the MVS-XIV. However, this "middleman" architecture is not critical to the invention, and a direct connection between the microprocessor 20 and a foot pedal 68 with conventional interface circuitry may also be used. With the MVS-XIV present, however, the aspiration vacuum is generated to support the operation being performed with the probe. This vacuum is coupled by a vacuum line (not shown) to the probe 22.

The microprocessor 20 performs a scaling operation in the main software loop to be described below using data from the foot pedal 68 and from the maximum power control 64. The data from the foot pedal 68 is a number representing the percentage of full-scale deflection of the foot pedal. The data from the maximum power control 64 indicates the desired full power level set by the user for 100% deflection of the foot pedal. The microprocessor 20 simply combines these two numbers to determined the percentage of full-scale power currently desired by the user. This number is then output on the bus 62 to the linear programmable amplifier 60. This amplifier amplifies the driving signal on the line 58 and outputs it at the desired amplitude level on a line 72. In the fixed power embodiments such as is shown in FIG. 19, the digital word on bus 62 will be fixed, or, in some embodiments, will be one of a selected number of possible gain level steps available to the user.

The driving signal on line 72 is generally a sinusoid having an RMS voltage level related to the desired power dissipation. This signal is applied to the input of a power operational amplifier 74 for amplification in a class AB mode.

The output of the amplifier 74 is applied to the primary of a voltage step-up transformer 76. A current-sensing resistor 78 is in series with the return line from the primary of the transformer to the operational amplifier 74. The secondary of the transformer 76 is coupled to the line 34 and a line 80. The line 80 is coupled to one end of the coil C on the tuning inductor. The other terminal of coil C is coupled to one terminal of coil A. The other terminal of coil A is coupled via a line 32 to one terminal of the crystals 28 and 30 (which are coupled in series). The line 34 is coupled to the return side of the piezoelectric crystal 30. Thus the current flowing in the secondary of the step-up transformer 76 is the series current flowing through the crystals 28 and 30 of the probe 22. Note that this current also flows through the tuning inductor coils A and C.

Since the voltage waveform on line 72 is in phase with the voltage waveform across the primary of the step up transformer, the phase detector 50 can sample the voltage on the line 72 with the assurance that the waveform on the line 72 is in phase with the voltage across the step up transformer. To determine the relative efficiency of power transfer from the driver to the probe, the phase angle between the voltage across the step up transformer primary and the current through the primary must be determined. The phase detector does this by comparing the phase of the voltage waveform on the line 72 to the phase of the current flowing in the primary of the step-up transformer 76, as determined by the voltage drop across the current-sensing resistor 78. The phase detector 50 is a conventional Motorola integrated circuit or any eguivalent which is commercially available.

The magnitude of the phase angle error is indicated by the width of the pulses on lines 84 and 86. The purpose of the integrator 52 is to average out the pulses over time so that the system has a smooth D.C. response to changes in the phase angle. The A/D converter 54 converts the analog phase angle error signal to a digital phase angle error word on bus 48.

The microprocessor 20 perform the linear power control, impedance-matching, and frequency-tuning functions of the invention by running a program stored in local RAM 90. This memory also includes ROM for storage of look-up tables and other information which does not change over the life of the system.

Referring to FIG. 3, equation (A), there is shown the expression which defines the relationships which exist when the piezoelectric crystals are being driven at the resonant frequency of the mechanical system (equation A). Equation B in FIG. 3 defines the value of the tuning inductance when it is in the tuned condition when the crystals are being driven at the resonant frequency of the mechanical system. Equation A represents the expression for the resonant frequency of the mechanical probe system for any particular temperature.

Figure 2I:
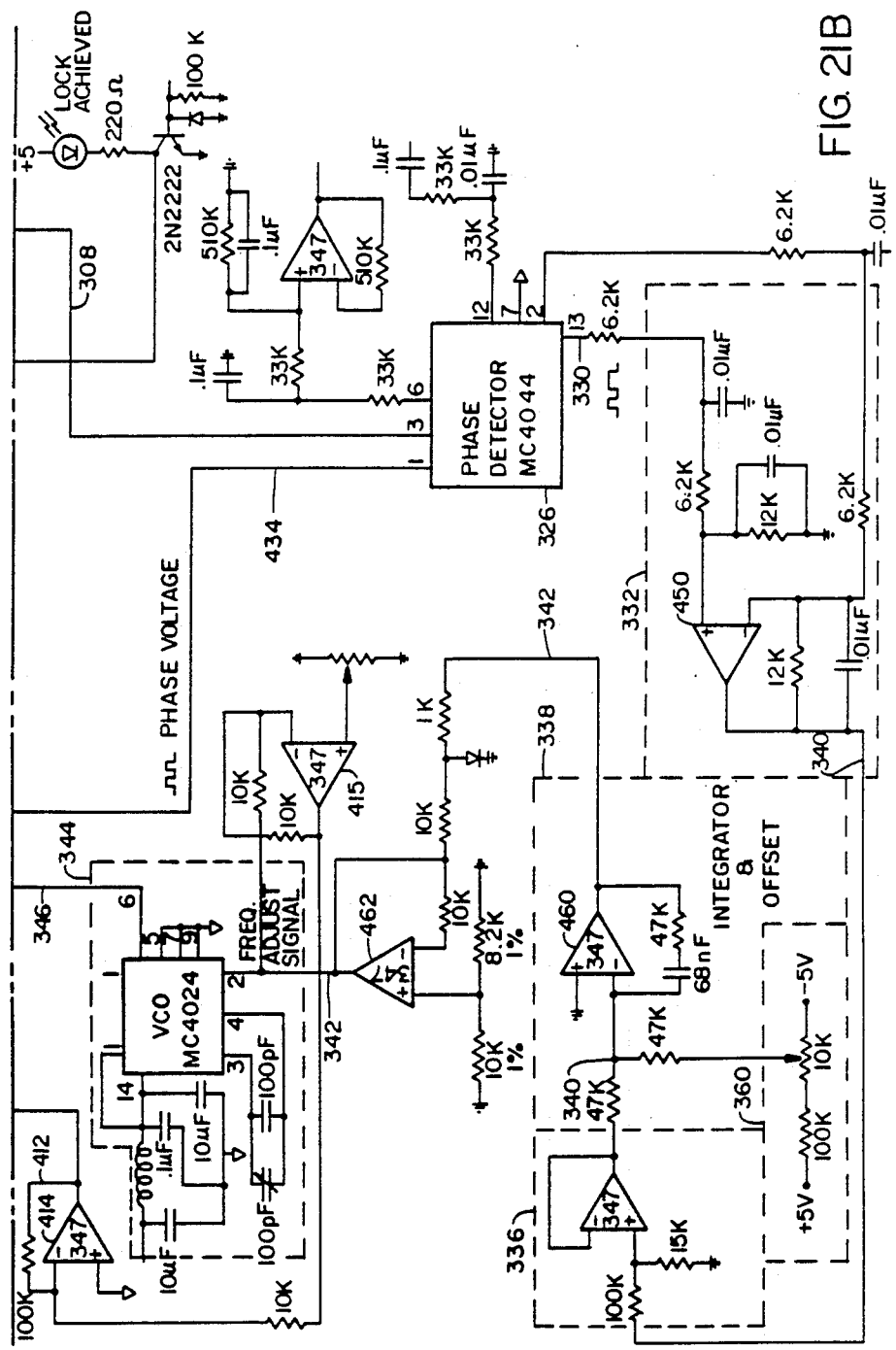
FIG. 2 is the simplified equivalent circuit model used to explain the operation of the probe and tuning inductor system.

In FIG. 2, the mechanical system is represented by the components in the equivalent circuit, labeled $R_S$, $C_S$, and $L_S$. The value of the component $R_S$ represents the mechanical load engaged by the tip of the probe. The component $C_S$ represents the elasticity of the metal in the probe. The component $L_S$ represents the mass of the probe. The value of the components $C_S$ change with changing temperature. The temperature may change either because the ambient temperature changes or because of power dissipated in the probe through excitation of the crystals. The value of the component $R_S$ changes greatly with the loading of the probe.

The other components of the crystal/probe system equivalent circuit are $C_P$ and $R_p$. The component $C_P$ represents the parallel electrical capacitance of the crystals 28 and 30 in FIG. 1. The component $R_P$ represents the leakage of electrical current between the terminals of the crystals, i.e., the current leakage from line 32 to line 34.

At the mechanical resonance frequency, the reactive component represented by $C_S$ (jw $C_S$) is exactly equal to and opposite in sign to the reactive component $L_S(1/jw\ L_S)$. Since these two reactive components cancel each other out, the eguivalent circuit for the crystal/probe system is as shown in FIG. 4. As can be seen from FIG. 4, the equivalent circuit has a substantial capacitive reactance of the crystals 28 and 30. Thus the load impedance has a real component represented by the value of the resistors $R_S$ and $R_P$ in parallel, and a reactive component of a capacitive nature represented by the capacitance $C_P$. According to the teachings of the invention, maximum power efficiency will be achieved by tuning the tuning inductor $L_T$ so as to cancel out the reactive component and the load impedance represented by $C_p$. When the crystals 28 and 30 are driven at the resonant frequency of the mechanical system for any particular temperature, the necessary value for the tuning inductance is given by equation B in FIG 3.

As can be seen from equation B, the value for the tuning inductance is highly dependent on the value for the resistive components $R_S$ and $R_P$ and upon the value of the parallel electrical capacitance of the crystals 28 and 30. This means that the necessary value for the tuning inductance to keep the probe system in proper tune will change with changing temperature, changing loading conditions, and changes in the level of power dissipated in the probe by the driving system. The reason for this is that either changes in ambient temperature or power dissipation in the probe raises the temperature of the probe and therefore affects the elasticity of the material. This changes the value of the component $C_S$ in the eguivalent circuit of FIG. 2 and therefore changes the mechanical resonant frequency as defined by equation A of FIG. 3. Changing loading conditions also change the mechanical resonant frequency because, in addition to changing the value of $R_S$ in FIG. 2, changing load also affects the value of $L_S$ because the load becomes an effective part of the mass of the system. This also changes the value of the mechanical resonant frequency defined by equation A by FIG. 3.

The teachings of the invention regarding tuning out the capacitive reactance of the crystal/probe system, when operating at its resonance frequency, may be implemented in at least two ways. One way is a coarse-tuning-only process, and the other way is a coarse-tuning process followed by a fine-tuning process. In one embodiment, the value of $L_T$ is adjusted to the level defined by equation B in FIG. 3 using a two-step process. The first step in this process is a coarse-tuning process where the phase angle error word on line 48 is used to generate an address into a look-up table. This look-up table will have stored therein experimentally determined values for the phase angle which result from various power levels. The overall effect of changes in the equivalent circuit component values with changing power levels is to alter the magnitude of the overall load impedance and its phase angle relative to its real component. The reactive component of the load impedance also changes, thereby destroying the reactive component cancelling match with the source impedance. This alteration in the match of the two impedances changes the phase angle. Unless $L_T$ is changed in response to these changes, the probe will be out of tune and maximum power transfer efficiency will not be maintained.

The system of the invention uses the phase angle change resulting from the above-noted changes as an index into a look-up table from which data is obtained which defines the necessary magnitude of the tuning inductor for that phase angle condition to keep the system tuned for maximum performance. The look-up table contains experimentally determined data which defines the optimal magnitude for the inductance of the tuning inductor for a given phase angle, or power level, or temperature, or some combination of the three. Although in some embodiments the look-up table adjustment alone may be sufficient, in one embodiment, a further adjustment is made to fine tune the inductance of the tuning inductor to bring the phase angle to zero or some other predetermined acceptable level of phase angle error. The second stage in this process of tuning the tuning inductor involves incrementing the D.C. bias level of the flux modulating coil and testing the phase angle. This process is continued until the phase angle reaches the predetermined acceptable angle. The user can set any acceptable level for the phase angle including zero.

Figure 5:
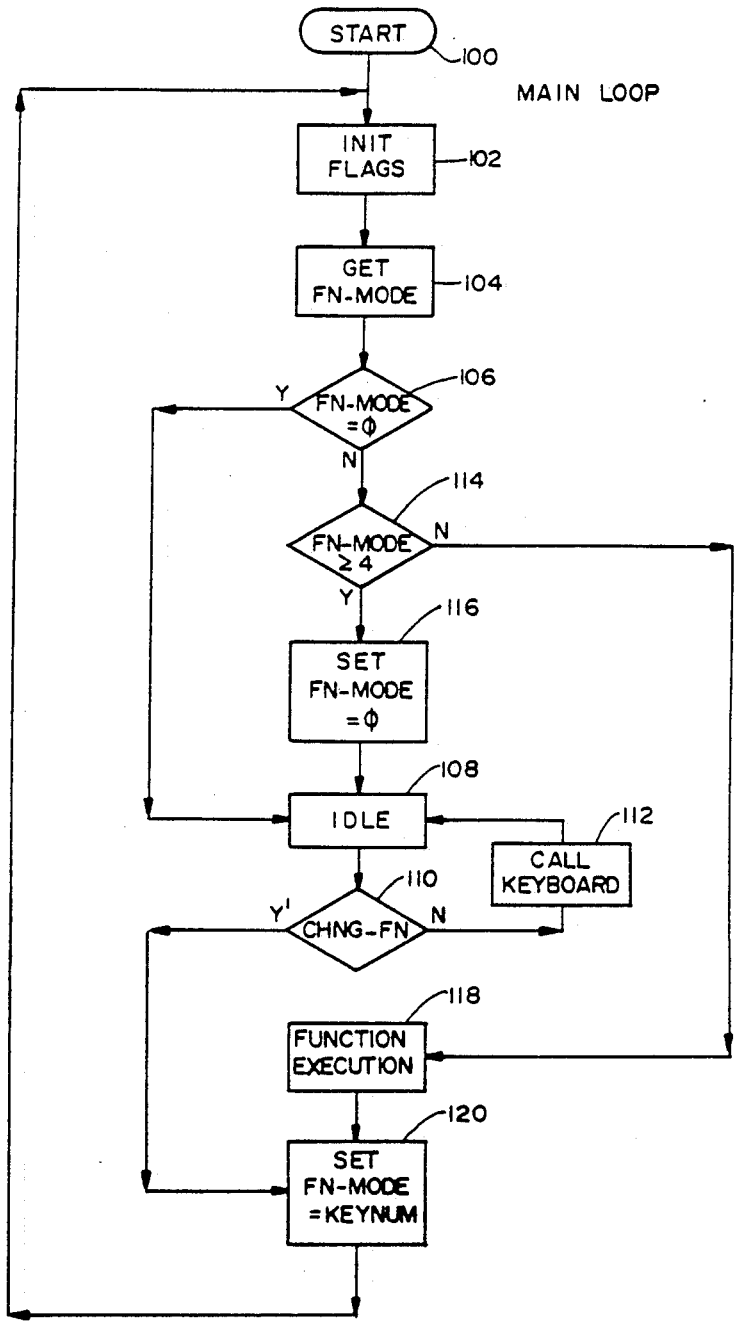
FIG. 5 is a flow diagram of the main loop of the control program that controls operations of one embodiment of the invention.

Referring to FIG. 5, there is shown a flow chart for the main loop of the software run by microprocessor 20. The purpose of the main loop of the program is: to establish the mode in which the system is to operate; to monitor the functions of the system; to provide audio responses to the user's manipulation of various controls; to handle display data on the front panel; to communicate with any system coupled to the serial port; and to perform any necessary mathematical computations such as foot pedal position scaling.

Main loop processing begins at power-up time in block 100. From there processing proceeds to block 102, where various system flags are initialized. These flags indicate the status of various conditions in the system, such as error conditions and so on, for the various functions of the system.

processing then proceeds to block 104. In this block, the microprocessor reads the data from a buffer which contains I/O data from the function switches on the front panel. When the function switches are manipulated by the user, interrupts are generated which cause the function switches to be read by the microprocessor. Data obtained in this I/O operation is then stored in a buffer in the RAM 90 in FIG. 1. Block 104 reads this portion of memory to obtain the data and determine which function the user desires. The user can select a fixed power mode where the maximum power setting on the front panel is sent to the probe 22 or a linear power control where the desired percentage of the maximum power is sent to the probe 22.

Processing then flows to block 106. This block represents a test of the data obtained regarding the desired function. If the function data is zero, processing goes to block 108, where the machine idles waiting for something to happen. This idling occurs by continuous looping to a test block 110, where the microprocessor reads the contents of the function mode buffer and determines if there has been a change in the desired function. If there has not been a change, processing flows to block 112, which is a call to the keyboard reading subroutine. This subroutine addresses the function or mode keys on the front panel and reads the data describing their current status. This data is then written into the function mode buffer. Processing then returns to block 108.

Returning to block 106, if the test of the data in the function mode buffer indicates that the desired mode is not equal to zero, processing proceeds to the test of block 114. The purpose of block 114 is to determine whether the function mode data is equal to 4 or greater. Such function modes would be illegal and are filtered out. This filtering is done by block 116 when the answer to the test of block 114 is yes. In block 116, the data in the function mode buffer is cleared to zero, and processing proceeds to the idle block 108.

If the test of block 114 indicates that the function mode is not equal to 4 or a larger number, processing flows to block 118, where the function is executed. Function execution is simply a series of calls to subroutines which will be described when the interrupt service routines are described. Function execution also includes performing the scaling function on the foot pedal data.

After said execution, processing flows to block 120. Processing can also flow into block 120 from block 110 if the answer to the test of block 110 as to whether the function data has changed is yes. The purpose of block 120 is to write the new function mode data with the key number that was obtained by the keyboard routine when the front panel switches were read. Processing then proceeds from block 120 back to block 102 where the loop is begun again. The microprocessor will continue to loop through the processing of FIG. 5 until an interrupt occurs.

Figure 6A:
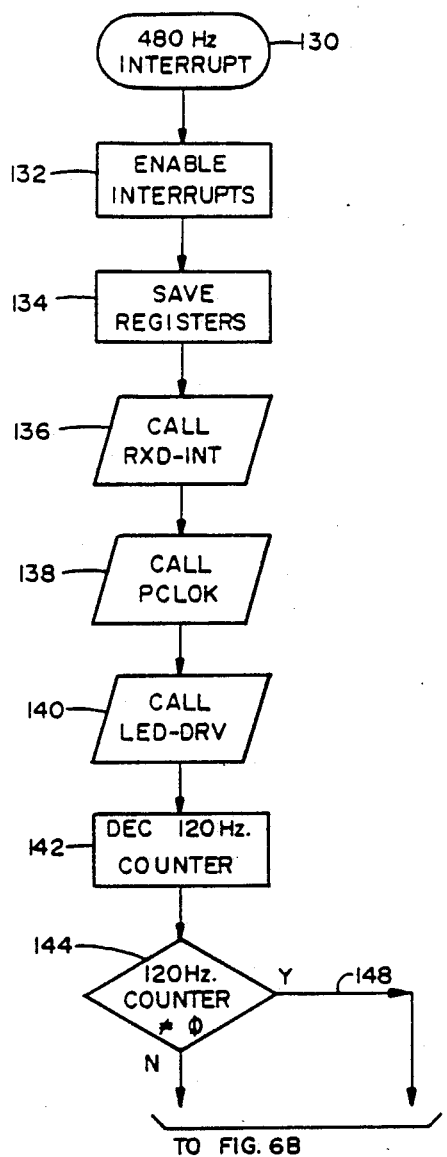
FIGS. 6A–6C are a flow diagram of the interrupt service routines of the control program of one embodiment of the invention.
Figure 6B:
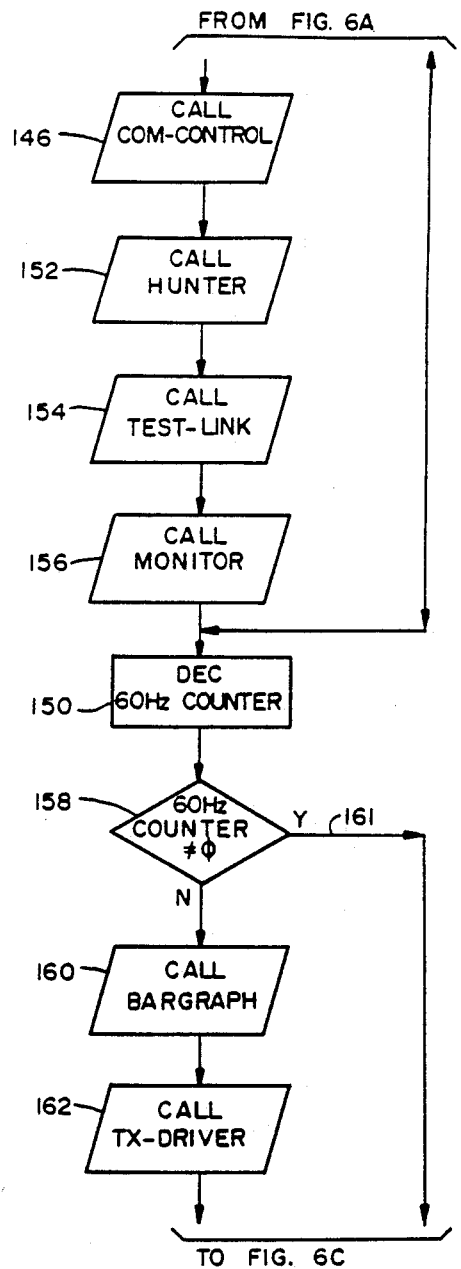
Figure 6C:
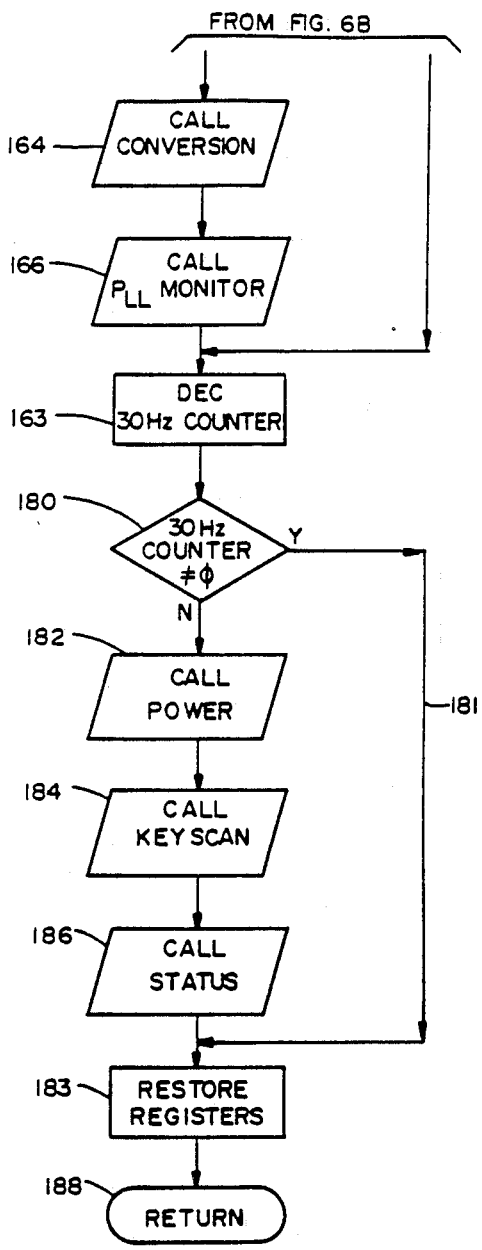
Figure 7:
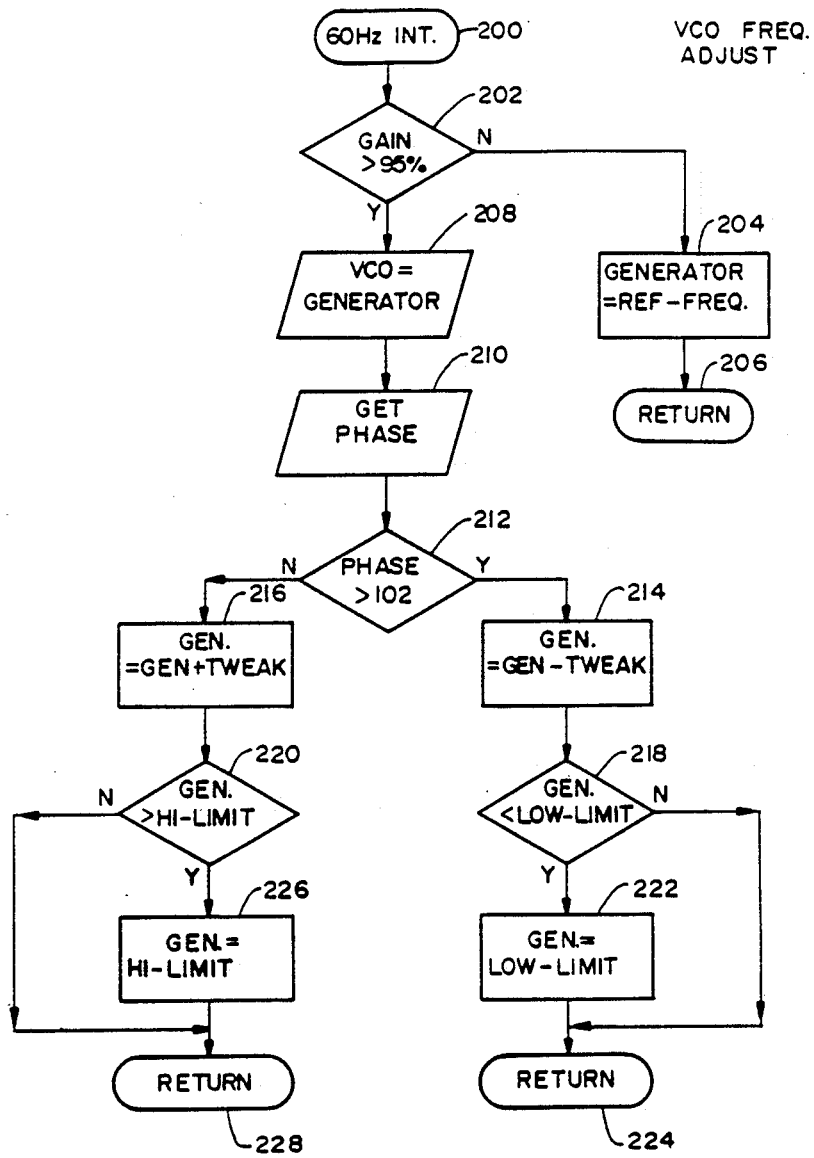
FIG. 7 is a flow chart representing further detail on the portion of the interrupt service routine that alters the VCO frequency to track changes in the mechanical resonant frequency of the probe in one embodiment of the invention.

Processing during interrupts is detailed in the flow chart of FIGS. 6A-6C and the flow chart of FIG. 7. The interrupts are generated by a multi-channel programmable counter. This counter is programmed to generate the interrupt represented by block 130, 480 times per second, i.e., 480 Hz. When this interrupt occurs, processing proceeds to block 132 where further interrupts are enabled. A prioritized interrupt scheme is used. Each time the 480 Hz interrupt occurs, each of the three other channels of the counter are incremented. These channels are programmed to generate interrupt requests at different counts. Each of these interrupts has its own service routine. Processing then flows to block 134 where the microprocessor registers defining its current status are saved in RAM for later recall after the interrupt service routine is processed. Processing then proceeds to block 136, where a subroutine is called to read the buffer storing any serial data which has arrived via the RS232 interface 70 in FIG. 1. The foot pedal position data comes in through this RS232 interface and will be accessed by the microprocessor 20 and the subroutine represented by block 136.

Processing proceeds from block 136 to block 138, which increments the system clock. From there processing proceeds to block 140, which represents a subroutine to call the light-emitting diode driver hardware and cause the proper light-emitting diode for the current mode to be lit.

Processing then proceeds to block 142, where the 120 Hz interrupt counter channel is decremented. There are three additional interrupt service routines which are performed less frequently than the interrupt service routine started at block 130. One interrupt service routine is performed 120 times per second. The remaining two service routines are performed 60 times per second and 30 times per second, respectively. They start at blocks 160 and 182, respectively. After decrementing the counter in block 142, the 120 Hz counter channel value is tested in block 144. The 120 Hz counter channel is a circular counter which will count down from a value of 120 by 1 every time block 142 is executed. Basically this occurs every fourth time the interrupt generated by block 130 occurs. When step 144 finds the count has reached zero, processing proceeds to block 146. Otherwise processing proceeds to block 150.

The block 146 represents the call to a communications control subroutine. This subroutine serves the same function as a telephone operator does in operating a switchboard to coordinate communications over the serial communications port of the microprocessor 20.

After block 146 is performed, processing flows to block 152 to call the hunter subroutine. The hunter subroutine tests a flag which give the status as to whether the probe is connected to the system. If the probe is not connected to the system, the hunter subroutine performs a sequence to attempt to reestablish the link.

Processing then proceeds to block 154, where a routine to test the link to the phacoemulsification probe is performed. Processing then proceeds to block 156, which calls a subroutine call monitor. The routine monitors error conditions and is not critical to the invention.

After the subroutine represented by block 156 is performed, a 60 Hz counter is decremented by block 150. The purpose of this step is to count the number of times the 480 Hz interrupt service routine has been performed, and on every eighth repetition, to perform the interrupt service routine starting at block 160. After block 150 is performed, block 158 is performed to test the value of the 60 Hz counter. If this counter value is zero, processing proceeds to block 160, which is a call to the bar graph subroutine. This subroutine addresses the bar graph display on the front panel and updates its status. This display is used to indicate the current power level. If the 60 Hz counter test of block 158 indicates the 60 Hz counter value is zero, processing will proceed along path 161 to a block 163. Block 163 decrements a 30 Hz counter and marks a test for the beginning of the interrupt service routine which is performed 30 times per second.

After block 160 is performed, the subroutine represented by block 162 is called. This subroutine calls the transmitter driver which sends data out the RS232 port to any systems which are connected thereto. Design of the system is modular, such that the system may be used alone or in combination with an MVS-XIV system and other systems in a family of products related to ocular surgery. The transmit driver also determines the rate at which information is sent to any other systems coupled to the RS232 port.

Next, the subroutine represented by block 164 is called. This is a subroutine which handles the A/D and D/A conversion processes needed to change the frequency, read the phase angle error, or tune the tuning inductor. In one function of the subroutine represented by block 164, the phase angle error word on bus 48 is read by the routine of block 164. This data is needed to do the modulating of the magnetic flux in the tuning inductor to keep the phase angle error at a predetermined value.

After the phase angle error word on bus 48 has been read, the system is ready to make any necessary adjustments in the D.C. bias current flowing in the flux modulation coil. This process is performed in a subroutine represented by block 166. The subroutine represented by block 166 actually performs two separate and independent functions in one embodiment. First, it tunes the frequency generated by the voltage-controlled oscillator 56 in FIG. 1 to change the frequency to correspond with the new resonant frequency for the probe, based on the then existing power levels, phase angle, temperature, or other such criteria. The details of how the frequency is adjusted are given in FIG. 7. As will be seen from FIG. 7, this is an iterative process.

To change the frequency of the VCO 56, the microprocessor 20 generates a digital word on bus 168 representing the desired amount of change. This word is then converted to an analog signal by D/A converter 170. This analog signal is output on line 172 to the VCO, where it causes the VCO frequency to be changed slightly from the frequency established by the voltage reference signal on line 174. A precision voltage reference source 176 generates the frequency controlling signal on line 174. The combination of the analog signals on line 172 and line 174 establish the new operating frequency for the VCO 56.

Figure 8:
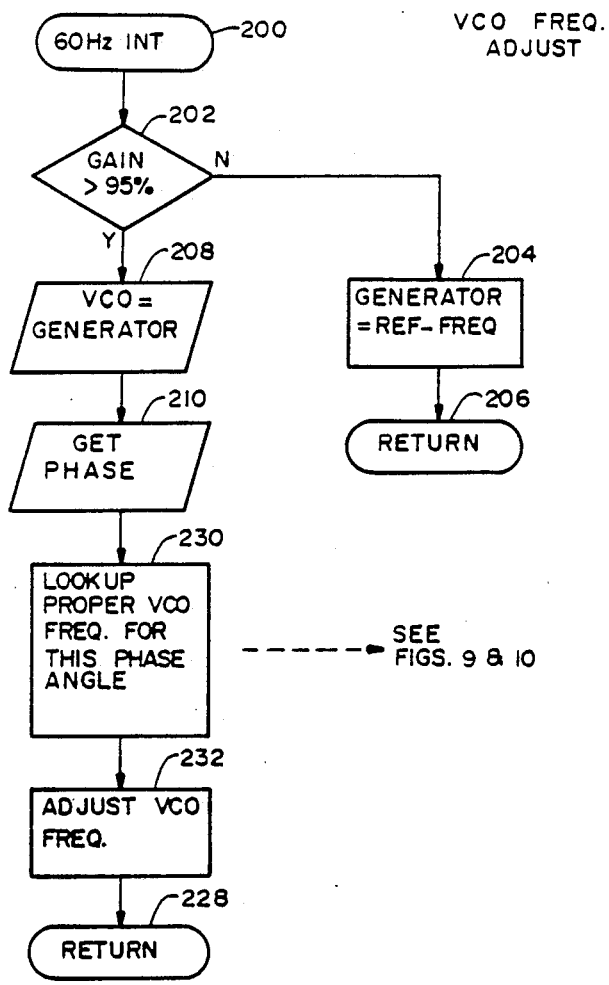
FIG. 8 is another embodiment of the VCO frequency tuning process according to an alternative embodiment of the invention.

The second thing that the subroutine of block 166 performs is the function of tuning the inductance of the tuning inductor to cancel the capacitive reactance of the probe. The flow chart defining the process by which this is done is shown in FIG. 8 and will be explained in more detail below.

In other embodiments such as those with fixed frequency and/or fixed power such as the embodiments shown in FIGS. 18 and 19, the subroutine of block 166 may only tune the tuning inductor.

After the subroutine of block 166 is performed, the 30 Hz counter channel is decremented by a count in block 163. In block 180 a test is performed to determine if the 30 Hz counter is or is not equal to zero. If the counter output is not equal to zero, a path 181 is transitioned to block 183. The process represented by block 183 is that of restoring to the microprocessor registers the values that they had when the 480 Hz interrupt occurred and the register contents were saved in the process of block 134. Processing may then resume from where it left off on the main loop.

If the test of block 180 indicates that the 30 Hz counter has reached zero, then block 182 is performed. This block represents the first step in the interrupt service routine which is performed 30 times per second. Block 182 is a call to the power control subroutine. This subroutine reads from memory or a buffer the power data which has been prepared for it by the function execution block 118 in FIG. 5 in the main loop. Part of the function of the execution block is to scale the data from the foot pedal to the maximum power level established at the front panel by the user. Therefore, if the maximum power dissipation level at the 100% foot pedal displacement position is to be 25 watts, and the foot pedal displacement is 10%, then the function execution block takes the 25 watt maximum power and multiplies it by 10% to derive a desired power level of 2.5 watts. The power routine represented by block 182 then determines whether or not the power level has to be changed from the current power level at which the probe is operating. In one embodiment there are four safety conditions which are checked before a power control word is output on the bus 62. If a change is necessary and the safety conditions are met, then the new power level desired by the user is transmitted as a digital number on the bus 62 as a desired gain for the linear programmable amplifier 60 in FIG. 1.

Next, the subroutine for scanning the keyboard is called, as symbolized by block 184. This routine performs I/O read operations and reads data from the keyboard and writes it into the mode buffer in RAM for use by the main loop. Note that this keyboard scan subroutine is shared by the interrupt service vector and by the main loop. Note that this keyboard scan subroutine is shared by the interrupt service vector and by the main loop. Next, the status subroutine is called, as symbolized by block 186. This subroutine checks various system status flags for conditions then existing in the system such as power, link present, error conditions, etc.

After block 186 is performed, the restore registers process is performed as symbolized by block 183, and the interrupts service routine terminates in block 188. This returns program control status to the main loop until the next interrupt occurs.

It will be apparent to those skilled in the art that not all the subroutines in the interrupt service routine shown in FIGS. 6A–6C are necessary for implementing the teachings of the invention. Specifically, only those subroutines necessary for linear power control, tuning of the tuning inductor, and changing the driving frequency for the probe to match the resonant frequency of the probe for various conditions are necessary and critical to the teachings of the invention. Further, each of these critical functions may be performed independently of the others in accordance with the teachings of the invention, albeit with lower power transfer efficiency and nonproportional power control in some cases. Specifically, the tuning of the tuning inductor to maximize power transfer efficiency may be performed independently of whether or not the power dissipated in the probe is controlled proportionately. Thus, the tuning inductor may be tuned for changing temperature conditions even at a fixed power level. Likewise, the frequency of the driving signal may be adjusted for changing mechanical resonance frequency regardless of whether or not the tuning inductor is tuned to maximize the efficiency of power transfer and regardless of whether or not the power levels of power dissipated in the probe are changed. Further, the power levels for power dissipated in the probe may be changed in proportional fashion regardless of whether or not the driving frequency is altered to compensate for changes in the mechanical resonance frequency. In some embodiments, the power levels may be changed linearly in response to user input regardless of whether or not the tuning inductor is tuned to maintain maximum power transfer efficiency throughout the power range. However, if the tuning inductor is not tuned, the transfer efficiency will change over the power range, and substantial linearity of power control may not be achievable over the full range of desired power dissipation levels.

Referring to FIG. 7, there is shown a flow chart for the frequency adjustment aspect of the teachings of the invention. As noted earlier, this particular subroutine is performed 60 times per second, as symbolized by block 200 and as implemented by one channel of the multi-channel counter (this counter may be in hardware or software). The first step is a test represented by block 202, which tests whether the current user-desired gain level is greater than 95%. This test is used in one embodiment such that frequency is adjusted only when gain levels are at levels greater than 95%. In other embodiments, this test may be omitted, and the frequency may be adjusted for all gain levels or may be adjusted for changing ambient conditions for a fixed gain level. In one embodiment, if the gain is less than 95%, processing flows to block 204. In block 204, the microprocessor 20 generates a frequency control word on the bus 168 which is converted to an analog signal voltage on line 172 by the D/A converter 170 to set the frequency of the VCO 56 at a known reference frequency. This reference frequency is the experimentally determined average mechanical resonance frequency of the probe at gain levels less than 95%. Processing then proceeds to block 206, where control is returned from the 60 Hz interrupt service routine to whatever processing sequence was interrupted.

If the answer to the test performed in block 202 indicates the gain is greater than 95%, processing proceeds to block 208. There the microprocessor reads the current contents of a variable called GENERATOR stored in the RAM 90. During the initialization process, the value stored in GENERATOR is the same reference frequency value used in block 204. However, during succeeding iterations through the 60 Hz interrupt service routine, the value of GENERATOR is altered in order to change the VCO frequency.

The purpose of this particular service routine for the 60 Hz interrupt is to alter the VCO driving frequency to track changes in the mechanical resonance frequency of the probe, which occur with changing gain levels and changing temperatures. The value stored in GENERATOR will determine the particular driving frequency generated by the VCO 56 in FIG. 1.

After the VCO frequency is set to the frequency dictated by the value of GENERATOR by block 208, processing proceeds to block 210, where the current phase angle error word on bus 48 is read. Next, in block 212, a test is performed on the phase angle error word read in block 210. In block 212, the phase angle error word is compared to a constant phase angle error, which is established by the user as the desired phase angle error when the system is in tune. This acceptable phase angle error will often be zero, but it need not always be so. In systems like that shown in FIG. 1, the phase angle error words on the bus 48 change around the number 102 as a center point representing zero phase angle because of use of a unipolar A/D converter 54. However, the system may be reprogrammed so that the number 102 is some other number representing the different phase angle about which the tuning of the VCO frequency is to be centered. In other embodiments, where a different type of A/D converter is used, the value used in testing the phase angle error word in block 212 may be different.

With the system of FIG. 1, if the phase angle error word on bus 48 is greater than 102, the value of GENERATOR will be decreased to change the phase angle toward zero. This process is done in block 214. Block 214 represents the process of accessing GENERATOR from RAM and subtracting from it a constant value called TWEAK, which is stored in a constants table in the RAM. The magnitude of TWEAK can be altered by the user by reprogramming the system. The value of TWEAK will set the step size by which the frequency changes are made, and therefore will control the response time and resolution of the system in adjusting VCO frequency for changed mechanical resonance frequency.

If the test of block 212 indicates that the phase angle error word is less than 102, then the value of GENERATOR must be increased by the value of TWEAK to increase the phase angle toward the test constant used in block 212. This process if performed in block 216 in the same manner as described for block 214. After the value of GENERATOR has been altered, the new value of GENERATOR must be tested against high and low limits to determine if it has been changed to an illegal, out-of-bounds value. The low limit test is symbolized by block 218, and the high limit test is symbolized by the block 220. If the answer to the test of block 218 is yes, indicating that GENERATOR has been changed to a lower value than the constant low limit, then block 222 is performed. In block 222, GENERATOR is set to the value of the low limit constant. If the answer to the test of block 218 is no, processing skips block 222 to block 224, where return from the 60 Hz interrupt service routine occurs.

A similar process is performed by block 226. Block 226 is performed if the answer to the test performed in block 220 is yes, indicating that GENERATOR has been increased beyond the value of the constant high limit. In block 226, the value of GENERATOR is set to the value of the high limit constant. Then processing proceeds to block 228, where a return from the 60 Hz interrupt service routine is performed. If the answer to the test of block 220 is no, then block 226 is skipped and block 228 is performed.

In alternative embodiments, a look-up table may be used for the frequency adjustment instead of the iterative approach shown in FIG. 7. In such an embodiment, the steps following step 210 in FIG. 7 would be replaced by a single step of using the phase as an index into the look-up table stored in ROM to derive a value to send out on bus 168 in FIG. 1. This value would be experimentally determined for that particular phase angle and would establish the driving frequency at the mechanical resonance frequency that experiments showed resulted in that phase angle. The flow chart for such an embodiment is illustrated in FIG. 8. The step 30 represents the process of looking up the proper VCO frequency for the phase angle read in step 210. This process involves generating an address using the phase angle error word on bus 48 as an index and then accessing the frequency correction data in the look-up table and storing it in a buffer. Step 232 represents the use of the frequency correction data from the look-up table to generate the proper word on the bus 168 in FIG. 1 to cause the voltage-controlled oscillator 156 to assume the frequency of the new probe mechanical resonance frequency. Step 228 represents the return from the interrupt service routine.

In yet another alternative embodiment, the step 230 in FIG. 8 can represent the look-up of the proper VCO frequency from one of several look-up tables. These look-up tables could be differentiated based upon the amount of time for which power has been applied to the probe. That is, each look-up table could contain the experimentally determined values for the probe resonant frequencies after the probe has been operated for a specific time and, possibly, at specific power levels. These different tables would contain the different experimentally determined mechanical resonant frequency values for the probe operating at different temperatures resulting from the measured time at certain power dissipation levels. In yet another alternative embodiment, an actual temperature sensor on the probe could be used. The microprocessor 20 could measure the probe temperature periodically when tuning of the driving frequency was necessary. This temperature could be used as an index to determine which look-up table to use. Once the proper look-up table is determined, either from the time for which the probe has been operating or the temperature of the probe, the phase angle or the temperature or some other variable indicative of the shift in mechanical resonance frequency may be used as an index to access the proper value in the look-up table. These alternative embodiments are illustrated in FIGS. 9 and 10, which represent breakdowns of the steps performed in block 230 for the different embodiments.

Figures 9, 10:
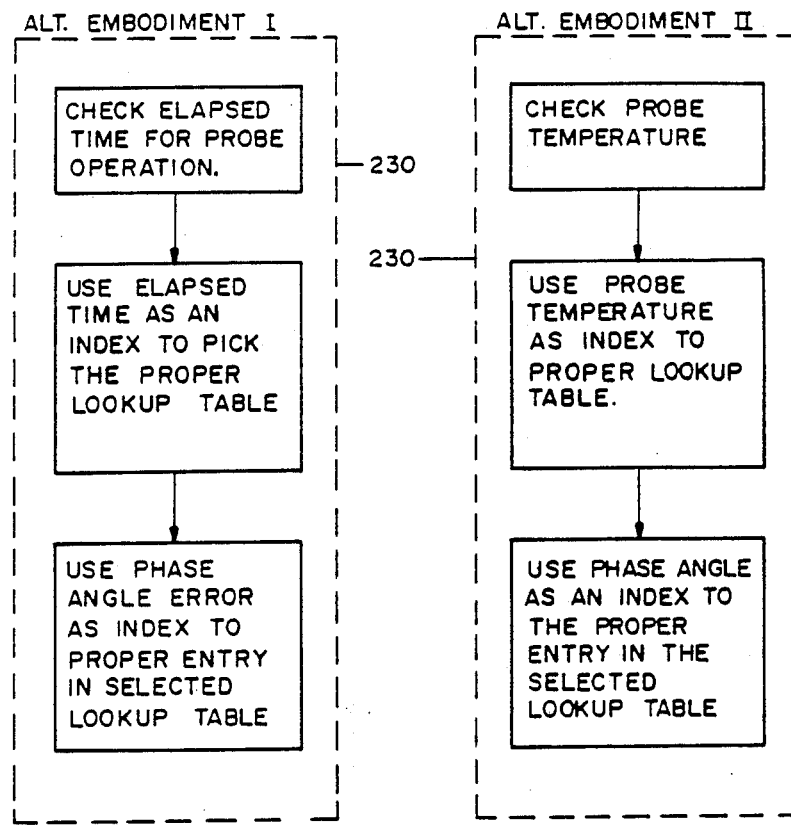
FIGS. 9 and 10 are alternative ways of performing step 230 in FIG. 8.

With respect to the embodiments shown in FIGS. 8-10 for adjustment of the VCO frequency, it should be noted that this process may occur independently of the process of tuning the tuning inductor 36 in FIG. 1. That is, the processes of FIGS. 8-10 may be performed for a fixed tuning inductor which is adjusted to cancel the reactive component of the load impedance at a specific operating temperature or gain level. At different operating temperatures and/or gain levels, the probe may be slightly out of tune by virtue of the inability to change the value of the tuning inductance, but the VCO frequency may be altered to match the changed mechanical resonance frequency for the new conditions, even though a zero phase angle cannot be achieved. That is, according to the teachings of the invention, VCO frequency alteration to track the mechanical resonance frequency drift works whether or not the tuning inductor value is changed. However, it works best when the value of the tuning inductor is changed to tune out the reactive component of the load impedance. The combination of these two adjustments by the system of FIG. 1 will insure that maximum possible power transfer efficiency is maintained over the entire power operating range of the system.

Likewise, the tuning inductor impedance may be altered to maintain proper cancellation of the reactive component of the load impedance independently of whether or not the VCO frequency is changed to track the drifting mechanical resonance frequency. The manner in which this may be done is illustrated in FIG. 11 in one embodiment.

Figure 11:
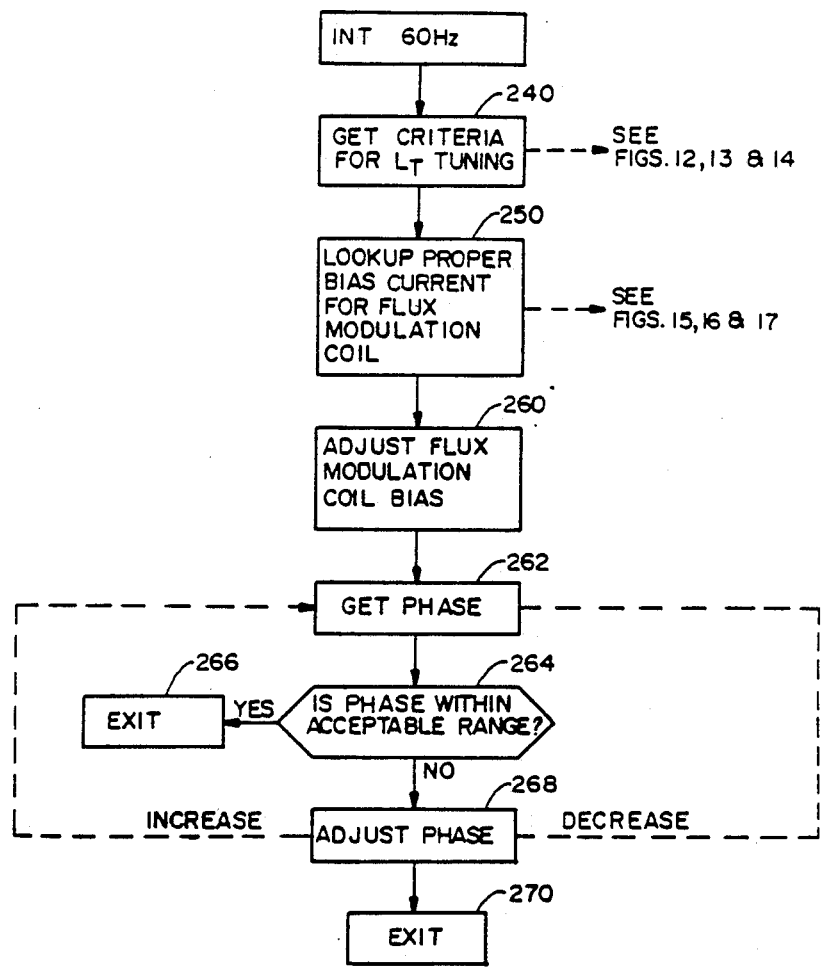
FIG. 11 is a flow chart for a process for tuning the inductance of the tuning inductor $L_T$ to cancel the reactance component of the load in one embodiment of the invention.
Figure 12:
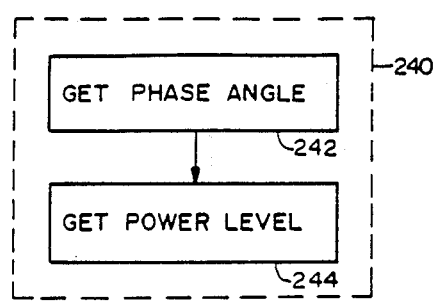
FIGS. 12, 13, and 14 are alternative ways of performing step 240 in FIG. 11.
Figure 13:
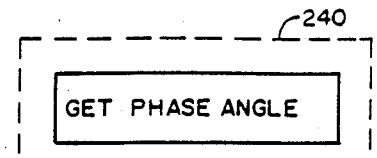

Referring to FIG. 11, there is shown the interrupt service routine for a 60 times per second interrupt to tune the value of the tuning inductor $L_T$. The function of the interrupt service routine of FIG. 11 is to tune out the reactive component of the load impedance represented by the probe. The first step in this service routine is represented by block 240. The process represented by this block is that of reading the proper criteria upon which the tuning of the tuning inductor will be based. In some embodiments, the criteria will be both the phase angle error and the power level. In such embodiments, block 240 represents the steps shown in FIG. 12. Step 242 in FIG. 12 represents the process of reading the phase angle error on the bus 48 and storing it in a memory location, and step 244 represents the process of reading the memory location which contains the current scaled power level obtained by scaling the deflection of the foot pedal 68 relative to the relative maximum power control setting 64 in FIG. 1. In other embodiments where only phase angle is used as the index, step 240 may represent only the process of getting the phase angle as shown in FIG. 13. In still other embodiments, step 240 may represent the step of obtaining the current power level, as shown in FIG. 14.

Figure 14:
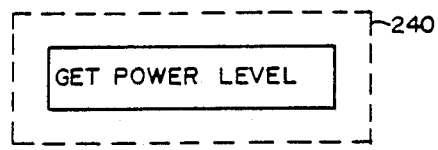

In both FIGS. 12 and 14, the step of getting the current power level may be omitted, and a step may be substituted of obtaining the current probe temperature via temperature sensor 92 and signal line 94 in FIG. 1.

Referring again to FIG. 11, after the criteria for tuning of the inductor $L_T$ has been obtained in step 240, a step 250 is performed. This step represents the process of using the criteria obtained in step 240 to look up the proper D.C. bias level for the flux modulation coil 44 in FIG. 1 to cause the tuning inductor to assume the proper inductance to cancel out the reactive component of the load impedance presented by the probe. Step 250 may represent the process of accessing a single look-up table wherein are stored experimentally determined D.C. bias current levels indexed by the criteria determined in step 240. In one embodiment, however, multiple look-up tables are used wherein the experimentally determined values in each look-up table are determined for a particular set of conditions. Typically, there will be one look-up table for a certain range of elapsed times during which the probe has been operated and another look-up table for another range of elapsed times during which the probe has been operated. In some embodiments, the look-up tables may be further divided in terms of the amount of time the probe has been operated at specific power levels, i.e., the total wattage which has been dissipated in the probe may be determined, and that wattage may be used as an index to the proper table based on the assumption that, after a given number of Watts has been dissipated in the probe, the probe will have achieved a predetermined temperature. In such embodiments, the look-up tables may be indexed by the range of watts dissipated in the probe for which the entries in the table are valid. Such an embodiment is illustrated in FIG. 15.

Figure 15:
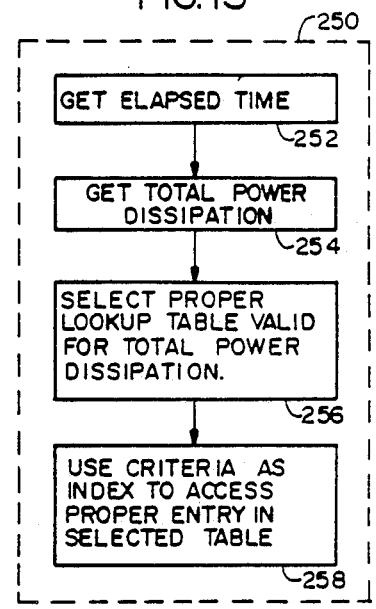

In FIG. 15, the first step is symbolized by block 252, where the elapsed time during which power has been dissipated in the probe is obtained. A step 242 represents the step of calculating the total power dissipation in the probe since its use began. This process may be an integration using the summation of the instantaneous average power level during each of a plurality of time slots multiplied by the increment of time for each time slot. This gives the total power dissipation as of the time step 250 is performed. Once the total power dissipation is determined, it is used in step 256 to point to the proper look-up table having bias current levels which are valid for that total amount of power dissipation.

Once the proper look-up table is selected in step 256, the criteria read in step 240 in FIG. 11 is used as an index to access the proper entry in the selected table. This entry will be the correct bias current for the flux modulation coil 44 to cause the tuning inductor to have the proper value to cancel out the reactive component of the probe load impedance for the particular total power dissipation up to that point.

Figure 16:
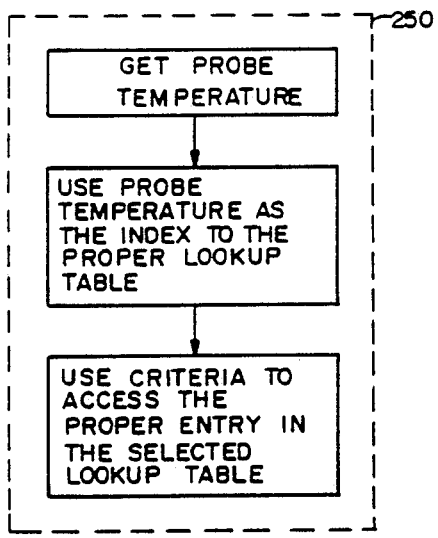
FIGS. 15, 16, and 17 are alternative ways of performing step 250 in FIG. 11.

An alternative and simpler embodiment is shown in FIG. 16. In this simple embodiment, the probe temperature is measured using the temperature sensor 92 shown in FIG. 1, and that temperature is used to select the proper look-up table. Each look-up table will cover a different range of temperatures for which its bias current entries are valid. Once the proper look-up table is selected, the criteria determined in step 240 is used to access the proper entry in that look-up table.

Figure 17:
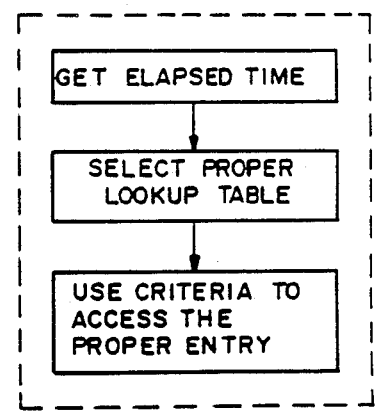

A still simpler embodiment uses only the elapsed time to select the proper look-up table. After the proper look-up table is selected, the criteria determined in step 240 is used to access the proper entry therein. This embodiment is illustrated in FIG. 17.

Returning again to FIG. 11, once the proper bias current entry has been selected from the proper look-up table, the flux modulation coil bias current is adjusted in step 260. This step represents the process of generating the proper digital word for transmission on bus 46 to D/A converter 40. The D/A converter 40 converts this number to an analog signal on line 42 which controls the amount of bias current flowing through the flux modulation coil 44.

Next a step 262 reads the phase angle error on the bus 48. This phase angle is then tested in a process symbolized by the block 264 to determined whether it is within an acceptable range defined by the user at the time of programming the system. In some embodiments, the acceptable range for phase angle error may be defined in real time by the user through the front panel.

If the phase angle is within the acceptable range, the service routine is exited in step 266, and processing resumes where it left off at the time the interrupt of FIG. 11 occurred. If the phase is not within the acceptable range, a step 268 is performed to adjust the phase in the proper direction by an incremental amount in similar fashion as shown in FIG. 7 for altering the GENERATOR constant by the constant TWEAK. That is, the phase angle error will be compared to the acceptable range and the direction of correction will be determined. The current word on the phase angle adjust signal bus 46 would then be added to a phase angle adjust constant, or the phase angle constant will be subtracted from the word on the phase angle adjust bus 46 depending on the desired direction of correction of the phase angle error. Thereafter, the interrupt service routine of FIG. 11 will be exited in step 270. In some embodiments, the adjust phase block 268 may cause looping back to step 262 to continue to loop through steps 262, 264, and 268 until exit step 266 is reached. These embodiments are symbolized by the dotted lines 272 and 274 in FIG. 11.

In other embodiments, the fine tuning of the phase angle represented by steps 262, 264, 268, and 266/270 may be omitted. In these embodiments, the phase angle adjust interrupt service routine is comprised solely of steps 240, 250, and 260, plus an exit step to return control to the point in processing where the interrupt occurred.

Finally, it should be noted that the proportional power control aspects of the teachings of the invention may be performed without either adjusting the phase angle through changing the inductance of the tuning inductor 36 and without changing the driving frequency generated by VCO 56. However, changing the power level to the probe without using at least the tuning inductor 36 to cancel out the changing reactance component of the load will not work very well, since at higher power levels, the probe temperature will begin to rise, and the system will become so far out of tune that it will be impossible to transfer enough power into the probe to maintain a linear or proportional relationship to the displacement of the foot pedal 68. However over small ranges of power dissipation levels, the system will work adequately with proportional power control without either tuning the tuning inductor or changing the VCO frequency.

That concludes the description of the digital embodiment of the teachings of the invention. There follows a description of an analog version of the teachings of the invention.

Figure 20:
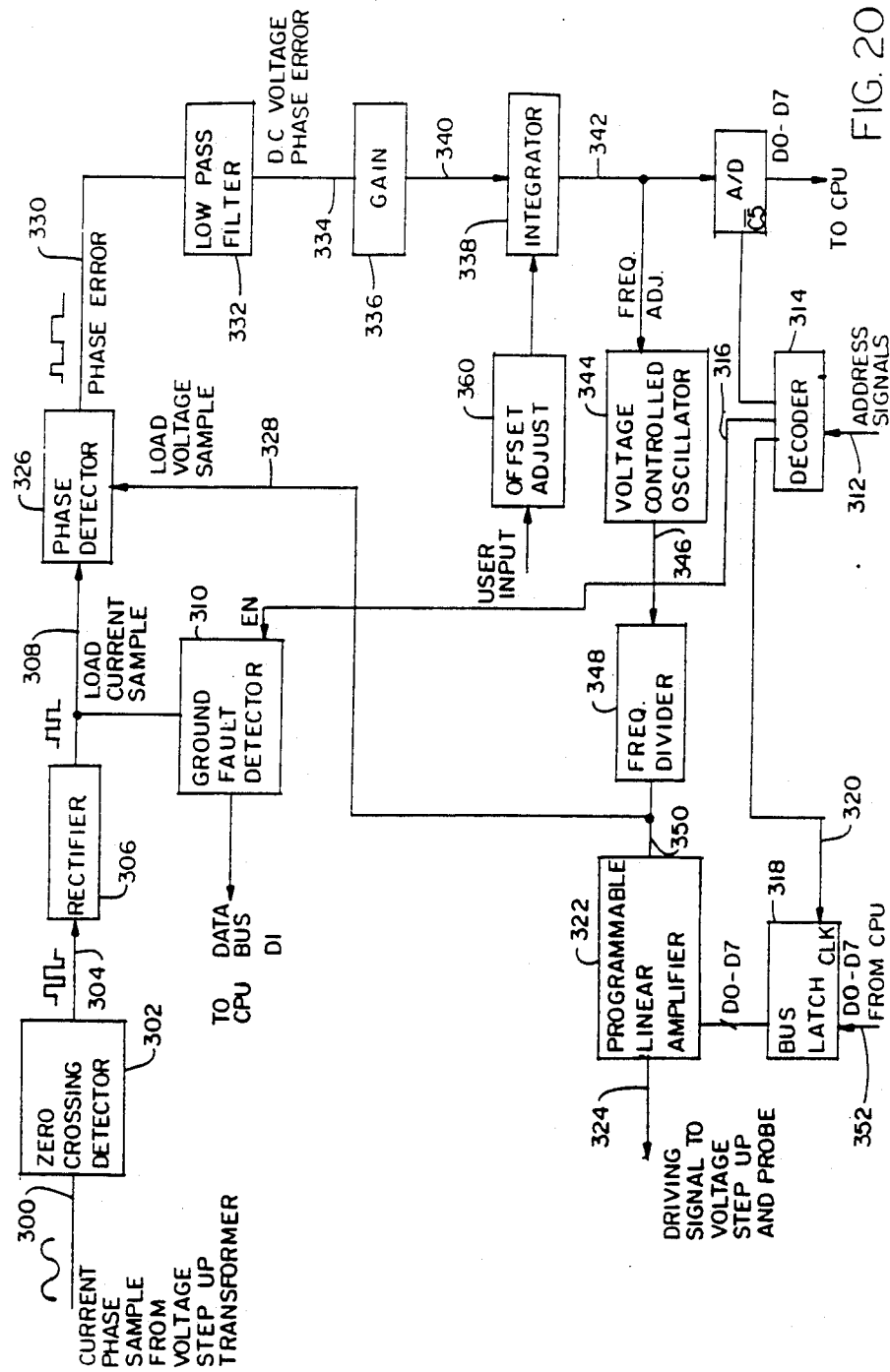
FIG. 20 is a block diagram of an analog embodiment of a subsystem to tune the VCO frequency to the mechanical resonance frequency using the phase angle as a criteria.

Referring to FIG. 20 there is shown a block diagram of an analog system for tuning the frequency of the driving signal for the probe. A sample of the current waveform through the probe enters the system on a line 300 where it is processed by a zero crossing detector 302. The zero crossing detector converts the current waveform to a square wave, alternating current waveform on a line 304. A rectifier 306 chops off one half of the square wave to convert the signal on line 304 to a pulse train of all positive or all negative pulses on line 308. A ground fault detector 310 monitors the signal on the line 308, and when no pulses occur on the line 308, a data bit D1 is latched to flag the failure of feedback from the probe. The computer (not shown) periodically addresses the ground fault detector via address signals on bus 312, decoder 314 and enable line 316 and reads the ground fault flag bit (D1). If it is set, the computer cuts off power to the probe by addressing a bus latch 318 via enable line 320 and address signals on bus 314 and by sending the proper data word to cause a programmable linear power amplifier 322 to cut off all driving signal power to the probe on line 324.

The signal on the line 308 comprises the load current sample needed by a phase detector 326 to determine the phase angle error or power factor caused by the current probe load impedance for existing conditions. The other signal needed for this determination is a sample of the phase of the voltage waveform for the voltage waveform used to drive the probe. This signal arrives on a line 328 which is coupled to the input of the programmable linear amplifier 322. The phase detector 326 compares the phase of the current waveform on line 308 to the phase of the voltage waveform on line 328 and generates a phase angle error signal on line 330. This phase angle error signal is in the form of a pulse width modulated pulse train where the pulse width is indicative of the phase angle error.

The phase angle error signal is passed through a low pass filter 332 to convert it to a direct current signal having a voltage which is indicative of the phase angle error on a line 334. This signal is applied through a gain stage 336 to an integrator 338. The purpose of the integrator 338 is to make the operation of the circuit not subject to offset errors intrinsic to operations with the operational amplifiers used to implement many of the stages shown in FIG. 20. Even the best operational amplifiers have some offset output voltage for a zero volt differential input. This offset error would exist on the line 340, and if it were not eliminated, would be applied to the voltage adjust input of the voltage controlled oscillator used to generate the driving signal. This offset error would cause the driving frequency to always be slightly off from the desired driving frequency to match the mechanical resonance frequency. The integrator 338 acts as an infinite gain operational amplifier. When there is any voltage other than 0 volts on the line 340, the integrator 338 continually integrates (sums) it. This causes the output voltage of the integrator on the line 342 to continue to rise until the output voltage reaches the maximum voltage of one of the supply voltages to the integrator. This output voltage on line 342 is applied to the frequency control input of the voltage controlled oscillator 344 and causes the frequency generated by the voltage controlled oscillator to shift to the frequency corresponding the voltage on the line 342. This driving signal is output on the line 346 to a frequency divider 348. There it is divided down in frequency to the proper driving frequency for the probe. The linear power amplifier 322 then amplifies the signal on line 350 by the gain set by the computer via the data bus 352 and bus latch 318, and the amplified driving signal is output to the voltage step up transformer (not shown) via line 324.

Because the feedback is negative, the shift in frequency caused by the signal on the line 342 is such as to reduce the phase angle error signal on line 334. Thus if any offset error signal exists on line 340, the integration of the error and the negative feedback of the system will force the error signal on the line 340 to zero. Whenever the mechanical resonance frequency shifts because of changing conditions, the phase error signal which results therefrom will cause the integrator to force the VCO frequency to shift until the voltage on the line 340 is once again zero.

The phase angle error around which the system operates need not be zero. The user may adjust it to be some other value by use of the offset adjust circuit 360. This circuit forces the integrator 338 to tolerate a certain phase error.

Referring now to FIGS. 21A and 21B there is shown a more detailed shematic diagram for the analog embodiment of the teachings of the invention with respect to changing the VCO frequency in response to phase angle changes. The load current phase sample enters on line 300 on the upper right corner of FIG. 21A as the CURRENT PHASE signal. This signal is processed by a waveshaper in the form of operational amplifier 400. The output of the waveshaper 400 on line 402 is an alternating current signal having the frequency and phase of the current waveform through the load.

To get this signal in a condition to be read by a phase detector, the signal must be converted to a square wave, direct-current signal, i.e., it must be rectified and further waveshaped. To this end, the alternating current signal on line 402 is coupled to the negative input of an operational amplifier 404 which has its positive input coupled to analog ground and which acts as a zero crossing detector. The output on line 406 is a square wave, alternating current signal. A voltage divider comprised of resistors 408 and 410 change the maximum amplitude of the signal on line 406 to a level suitable for base drive of a transistor/diode rectifier circuit 306.

The rectifier circuit 306 converts the alternating current square wave on line 406 to a train of positive going pulses on the output line 308. This is done through use of the shunt diode 414 having its cathode coupled to the base of a transistor 416. The diode shunts all negative going pulses to analog ground. so that only the positive going pulses turn on the transistor 416 and drive line 308 to logic zero.

The computer (not shown) must know that the probe is present and is receiving the drive current to keep the driving signal power on, if the probe is not present, or the link to same is broken, the computer must shut off power to the probe as a safety feature since the voltage step up transformer steps up the driving voltage across the crystal to approximately 1000 volts. The computer must constantly monitor line 308 to determine if current phase samples are arriving. If they are, then the computer assumes that the probe is present and that the link to the probe is working. A retriggerable one shot 420 and a latch 422 are used for this purpose as the ground fault detector 310. The signal on line 308 constantly retriggers the retriggerable one shot 420 to keep its output on line 424 in a predetermined logic state constantly. When the pulses on line 308 stop, the retriggerable one shot emits a pulse on line 424 which is latched into the latch 422. This latch is periodically addressed by the computer by activating the read signal and writing the proper address to a decoder 314 to activate the 79H signal to the NOR gate 430. The computer then reads the contents of the latch 422, and, if the bit pattern is in a predetermined state, the computer knows that there has been a ground fault, and cuts off power to the probe.

To determine the correct frequency to use to drive the probe, the phase angle between the current waveform for current flowing through the crystals in the probe and the voltage waveform of the driving signal across the crystal and tuning inductor is used. This phase angle is circumstantial evidence that the impedance of the crystal/probe equivalent circuit has shifted away from the tuned condition where the combined tuning inductance and crystal/probe impedance appears to be purely resistive. When this happens, the mechanical resonance changes because the temperature changes have affected the elasticity of the probe metal thereby changing the equivalent circuit capacitance representing elasticity and changing load conditions have changed the effective mass of the probe. This alters the inductance in the equivalent circuit representing the mass of the system. The result is that the mechanical resonance frequency changes, so the driving frequency must be changed to keep the probe in tune. Further, the value of the tuning inductance should also be altered to keep the overall load impedance substantially purely resitive. The analog circuitry to alter the tunable inductance works the same as the circuit of FIG. 20, and will not be further detailed here.

To determine the phase angle, the signals on the line 308 are coupled to one sample input of a phase detector 326. This signal must be compared in phase to a sample of the voltage waveform across the tuning inductor and the crystal transducer of the probe. The voltage sample comes in on line 434 from the output of a counter/frequency divider 436 coupled so as to divide the output of the voltage controlled oscillator 344 down to the proper driving frequency for the probe (approximately 40 kilohertz).

The phase detector 326 generates a pulse width modulated phase angle error signal and outputs it on line 330. The pulse widths of the pulses in the signal on line 330 are proportional to the phase angle error. This signal is passed through a low pass filter 332 consisting of a passive network of resistors which shunt capacitors o ground and then through a gain stage consisting an operational amplifier 450 coupled as a low pass filter/integrator. The purpose of this low pass filter and integrator combination is to filter out high frequency noise components, and to convert the pulse width modulated phase error signal to a direct current voltage phase angle error signal on line 340.

After conversion of the phase angle error signal to a D.C. phase angle error voltage, the signal on line 340 is amplified in a gain stage 336. Thereafter, the D.C. phase angle error signal is applied to the input of the integrator 338. The purpose of the integrator is to eliminate the errors introduced by offset errors in the operational amplifiers preceding the integrator stage. As noted earlier, because of the high gain of the integrator and the negative nature of the feedback the integrator will force the frequency of the driving signal to change until the D.C. phase angle error signal on line 340 is zero volts.

The integrator 338 is comprised of an operational amplifier 460 coupled with capacitive feedback so as to act as an integrator. An offset adjust circuit 360 comprised of a voltage divider with a potentiometer as the second resistor is used to adjust the voltage on the line 340 so that any phase angle desired by the user may be used as the home point around which the integrator 338 forces servo action. That is, the offset adjust circuit 360 may be used to set some phase angle such as 5 degrees as the center point. Then when a phase angle of 8 degrees is found, the integrator forces a frequency change until the phase angle moves back toward 5 degrees. Likewise, if a phase angle of 2 degrees is found, the integrator forces the frequency to change until the phase angle once again is 5 degrees. However, the voltage on the line 340 will always be maintained at a Virtual ground level by virtue of the negative feedback whereby positive changes in the D.C. level of the phase error signal are applied to the negative input to the operational amplifier 460 which causes a change in the VCO frequency to reverse the direction of the change in the D.C. phase angle error signal. Any offset voltage on the line 340 will be continually integrator until the integrator output on line 342 reaches the power supply or "rail" voltage at which the integrator operates unless the phase angle change resulting from the changing voltage on the the line 342 acts to remove the voltage on line 340. The voltage on the line 342 then stabilizes at that voltage necessary to cause the phase angle error signal on line 340 to be zero.

The output of the integrator on line 342 is coupled through a level shifting stage comprising operational amplifier 462 which changes the level of the signal voltage to a level suitable for application to the voltage control input of the voltage controlled oscillator 344. The oscillator generates a driving signal having a frequency which is a function of the FREQUENCY ADJUST signal on line 342. The voltage controlled oscillator 344 has a characteristic curve of frequency versus voltage which has a less sensitive portion and a more sensitive portion. In the less sensitive portion, it takes more change of voltage on the line 342 to cause a one hertz change of the output driving signal frequency than in the more sensitive portion. The level of the signal on the line 342 is set to be in the low sensitivity portion of the characteristic curve of the VCO.

The output signal from the VCO is coupled via line 346 to the divider/counter 348. This counter divides the frequency on line 346 by a factor of 32, and outputs the lower frequency driving signal on line 350. This line is coupled to the input of the programmable linear amplifier 322.

The purpose of the programmable linear amplifier is to amplify the driving signal on the line 350 by a gain factor set by the computer (not shown) via the data bus 352. The programmable amplifier is comprised of several programmable switches 380, 382 and 384 which are coupled to the data bus via a bus latch 318. When the computer wishes to control the gain level, it activates the write signal WR and writes the address of the programmable amplifier on the address bus 312 and writes the desired gain control number on the data bus 352. This causes the decoder 314 to activate the enable signal on the line 390 thereby clocking in the gain control data on the data bus 352 via the NOR gate 392 and line 394 coupling the NOR gate output to the clock input of the bus latch 318.

The gain control number causes the programmable switches to control the resistor ladder networks 400, 402 and 404 in such a way as to set the desired gain level on line 406 at the input to the final gain stage 408. The final gain stage amplifies the signal by a fixed gain and buffers it from the output line 324 so that the resistor ladder network cannot be loaded down by external impedances coupled to the line 324.

For purposes of debugging, an analog to digital converter 410 is coupled by a line 412 to the output of the VCO through a pair of isolation and level shifting stages to sample the output amplitude level of the VCO. The A/D converter can be addressed by the computer to read the digital equivalent of the VCO output signal amplitude via the data bus 352 whenever the computer needs to know this value. This aspect of the circuit is not critical to the invention.

The analog method of tuning the VCO frequency may be used independently of proportional power control or of tuning of the tuning inductor impedance. Likewise it may be used with the digital methods of performing the latter two functions as disclosed above. In yet another embodiment the tuning of the tunable inductor may be done in analog fashion using a circuit using the same teachings of the circuit of FIG. 20.

For all embodiments where the frequency of the driving signal is to be tuned to the mechanical resonance frequency of the probe, there is an alternative way to determine the mechanical resonance frequency. In the embodiments discussed so far, the mechanical resonance frequency is inferred from the phase angle. That is, when conditions such as power level change resulting in temperature change or the load condition changes, the mechanical resonance frequency shifts and the phase angle is altered. Instead of measuring the mechanical resonance frequency itself, the resonance frequency is inferred from the resulting phase angle. This was done with either a lookup table as described with reference to FIG. 8 or by trial and error method as shown in FIG. 7.

Figure 22:
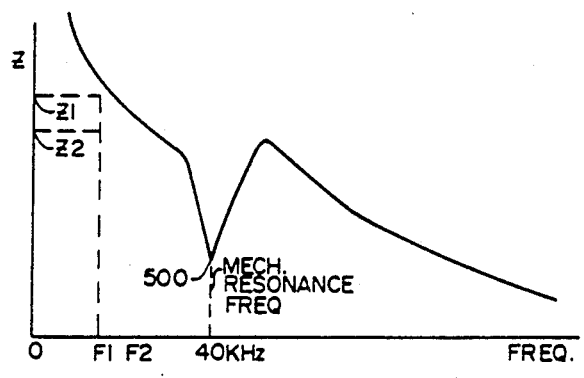
FIG. 22 is a curve showing the shape of the characteristic curve for the impedance of the probe at different frequencies surrounding the mechanical resonance frequency.
Figure 23:
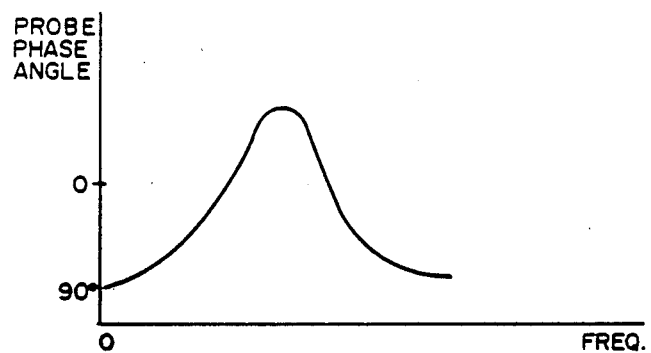
FIG. 23 is a curve showing the relationship of the phase angle to frequency for the phase between the voltage across the probe crystals and the current through the probe crystals for a given set of conditions.

Another way to determine the mechanical resonance frequency is to measure it directly using Ohm's law and the shape of the curve defining the load impedance represented by the probe. FIG. 22 shows the characteristic impedance of the probe without the tuning inductor over a range of frequencies surrounding the mechanical resonant frequency. The mechanical resonance frequency is always the frequency where the minimum impedance point 500 occurs from the equivalent circuit for the probe shown in FIG. 2. Since the impedance is higher at frequencies on either side of the mechanical resonance frequency, this fact can be used to determine the value of the mechanical resonance frequency under a given set of conditions. This can be done by measuring the current flowing through the probe at a number of different frequencies and finding the frequency where the current flow is a maximum. Once the mechanical resonance frequency is determined, the tuning inductor is tuned to reduce the phase angle to zero. FIG. 23 shows the relationship of phase angle to frequency for the phase between the voltage across the crystals and the current flowing through them under a given set of conditions.

Figure 24:
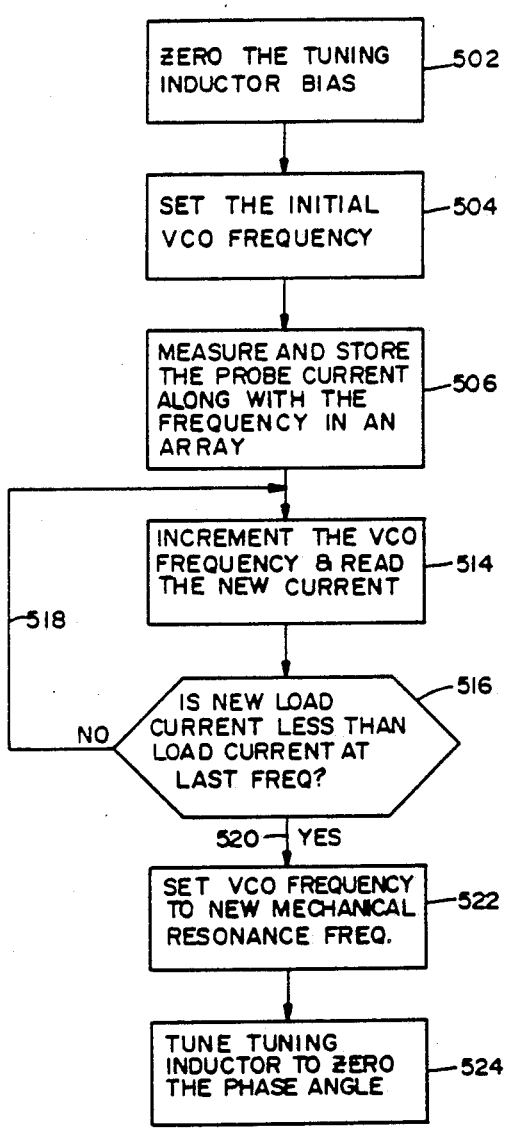
FIG. 24 is a flow chart for a method of using the shape of the characteristic curve for probe impedance to find the mechanical resonance frequency and to tune the tuning inductor for zero phase angle.

A method for tuning the probe for maximum efficiency of power transfer using the shape of the characteristic impedance of the probe as a pointer to the correct mechanical resonance frequency is shown in the flow chart of FIG. 24. The general idea is to sweep the VCO frequency through a number of frequencies on either side of the expected mechanical resonance frequency and read the current flowing through the probe at each frequency. The frequency at which the maximum amount of current flows is the mechanical resonance frequency. Once this frequency is determined, the VCO is set to this frequency, and the tuning inductor is biased to tune the phase angle to zero.

The first step in this process is to zero the bias of the tuning inductor 36 in FIG. 1 as symbolized by block 502. This entails having the microprocessor (or other analog circuitry controlling the bias of the tuning inductor) send a bias word on bus 46 to D/A converter 40 to reduce the bias current through the flux modulation coil 44 to zero. Next, an initial VCO frequency is set at some frequency less than the frequency of the impedance minimum 500 in FIG. 22. For the sake of example, assume this initial frequency if F1 in FIG. 22 which corresponds to a probe impedance of Z1. This step is symbolized by block 504 in FIG. 24, and is done by sending the proper frequency control word corresponding to frequency F1 on bus 168 in FIG. 1 to the D/A converter 170.

Block 506 represents the steps of measuring the load current drawn by the probe at frequency F1 and storing the value of the load current along with its frequency F1 in RAM 90 in FIG. 1. This done using the operational amplifier 508 in FIG. 1 along with rectifier 508 and A/D converter 510. The operational amplifier has one input coupled to line 82 which carries a signal voltage proportional to the magnitude of load current flowing through the crystals 28 and 30. The amplifier amplifies this A.C. signal and outputs it on line 509. The rectifier 508 converts the amplified load current signal on line 509 to a D.C. Voltage level proportional to the load current on line 511. This signal is converted to a digital word by the A/D converter 510, and makes the digital word representing the magnitude of the load current available on bus 512 for the microprocessor to read. The microprocessor 20 then reads the word on the bus 512 and stores it in RAM 90 along with the frequency which corresponds to this particular load current in memory.

The next step, as symbolized by step 514, is to increment the VCO frequency to a slightly higher frequency F2 corresponding to a load impedance Z2 and to read the resulting load current. The system then compares the load current read in step 514 to the load current stored in step 506 to determine if the new load current is less than the previous load current. This is done in step 516. Because it is known that as soon as the frequency is incremented to a frequency above the mechanical resonance frequency, the load impedance will begin to rise having reached its minimum at the mechanical resonance frequency, it follows that as soon as the load current begins to fall, the mechanical resonance will have been passed. The system then knows that the mechanical resonance frequency for existing conditions lies between the current frequency and the last used frequency. If the new load current is not less than the previous load current. Processing returns to step 514 to increment the frequency and to take another reading of the load current as symbolized by path 518. Then the test of step 516 is performed again.

If the new lead current is less than the old load current then the mechanical resonance frequency has been determined, and path 520 is taken to step 522. The next step is to set the VCO frequency at the frequency determined in step 516 to be the mechanical resonance frequency. This may he done by using the most current frequency or by interpolating between the current frequency and the last frequency used. If the step size is small, the current frequency may be used without appreciable error.

The final step is symbolized by step 524. In this step, the tuning inductor 36 is tuned in the manner described herein to zero the phase angle and make the load of the probe appear to be purely resistance. This can be done by a trial and error method by looking at the output of the phase detector, altering the tuning inductor bias and looking again at the output of the phase detector. Alternatively, the proper bias level to zero the phase angle for the current conditions of frequency, probe temperature, etc. can be looked up in a look up table. The value which emerges from the look up table can then be used to set the bias level for the current through the flux modulation coil of the tuning inductor.

Figure 25:
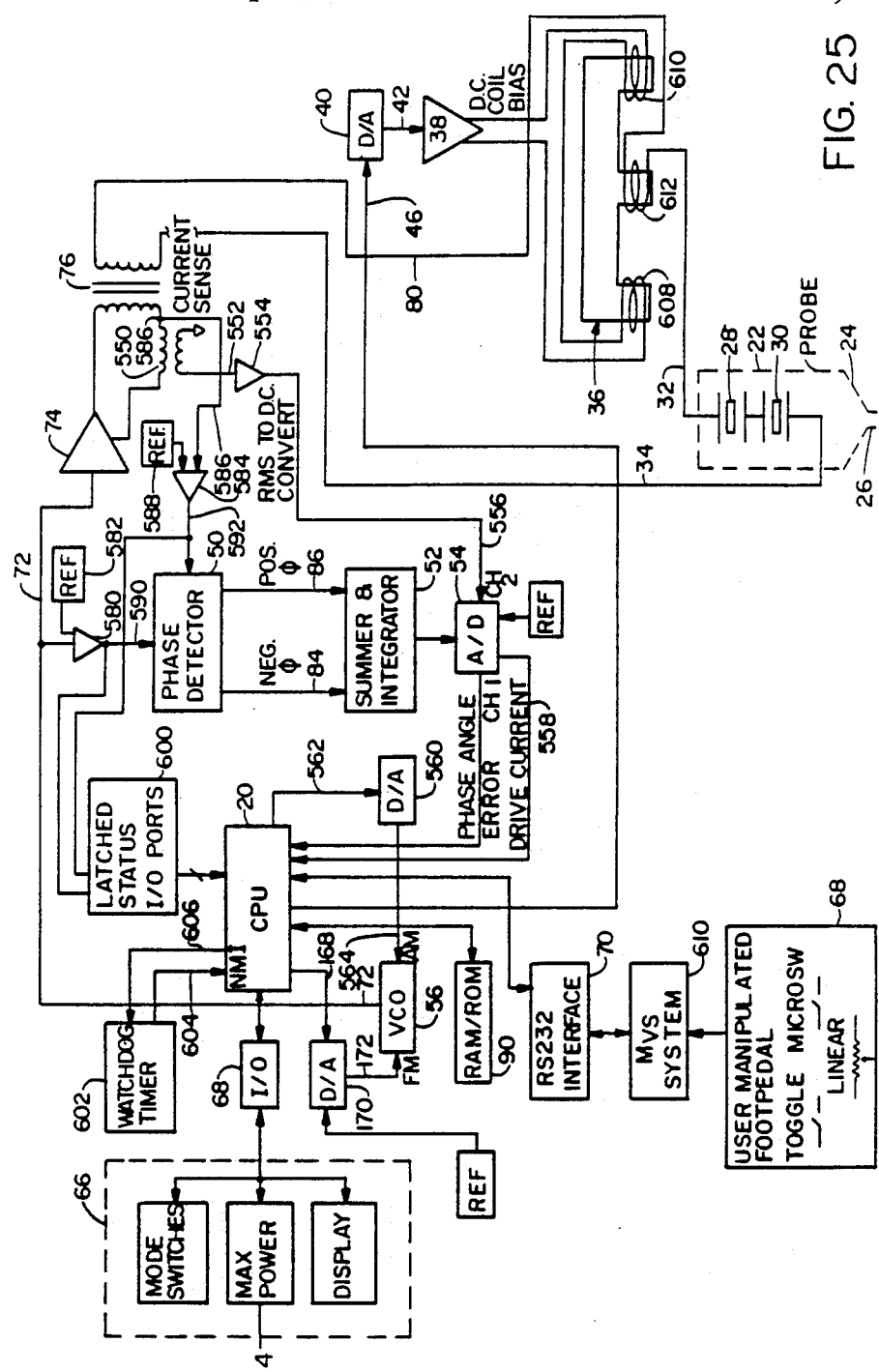
FIG. 25 is a block diagram of the hardware of the preferred embodiment of the invention.

Referring to FIG. 25, there is shown the preferred embodiment of the circuitry of the invention. The embodiment shown in FIG. 25 is substantially similar to the embodiment shown in FIG. 1 except that certain changes have been made. These changes will be described in detail. Portions of the circuitry that are identical between the embodiment of FIGS. 1 and 25 and which serve the same function in both embodiments are identified with like reference numerals in both figures. The discussion of the common elements of the circuitry given above is equally applicable to the embodiment of FIG. 25 and will not be repeated here.

The first change of significance is the substitution of a current sense transformer 550 for the current sense resistor 78. This current sense transformer has its primary in series with the primary winding of the voltage step up transformer 76. The current sense transformer 550 is, itself, a voltage step up transformer such that the voltage generated across the primary winding by the current flowing through the primary of the voltage step up transformer 76 generates a voltage in the secondary of the current sense transformer 550 which is a multiple of the voltage across the primary. The multiple depends upon the turns ratio as between the primary and the second windings of the transformer 550. The current sense transformer 550 has less parasitic inductance and parasitic capacitance than the current sense resistor 78 which eliminates one possible source of error in determining when the frequency of the driving signal is most closely matched to the mechanical resonant frequency of the probe. Since the software uses the voltage swings on the secondary of the current sense transformer 550 as part of the information needed to determine the phase angle, it is important to derive clear signals with a high signal to noise ratio. The current sense transformer 550 improves the signal to noise ratio by stepping up the voltage across the primary winding of the transformer 550 to a level well above any noise.

The R.M.S. value of the A.C. signal on the line 552 is converted to a D.C. signal value by an operational amplifier 554. The magnitude of this signal indicates the amplitude of the current flowing in the primary of the step up transformer 76 and therefore is indicative of the level of drive current in the probe 22. This D.C. signal on line 556 is coupled to one input of a two channel analog-to-digital converter 54. The analog-to-digital converter 54 converts the D.C. level on line 556 to a digital signal on the bus 558 which indicates the level of the drive current flowing in the primary winding of ;he step up transformer 76. This information is used by the sweeper software routine to be described below in determining the frequency of drive signal on line 72 which matches the mechanical resonance frequency of the probe 22.

When the CPU 20 determines the proper driving frequency, a digital frequency control word is written via bus 168 to a D/A converter 170. This word is converted to an analog signal level on the line 172 which is coupled to the frequency modulation control input of the voltage controlled oscillator 56. The voltage on the signal line 172 controls the frequency of the driving signal generated by the VCO 56 on the line 72.

The amplitude of the driving signal on line 72 is controlled by the CPU 20 via a digital-to-analog converter 560. The CPU 20 receives signals from the user manipulated footpedal 68 Via the RS232 interface 70 regarding t he level of power the user desires to be sent to the probe. The CPU 20 converts these signals to a digital word which corresponds to the desired level of power and sends this word out to a digital-to-analog converter 560 via a bus 562. This unit converts this desired power level word to an analog signal having an amplitude which corresponds to the desired level of power. This analog signal is coupled on line 564 to the amplitude modulation input of the VCO 56. The analog signal causes the VCO 56 to generate a drive signal having an amplitude on the line 72 which corresponds to the desired level of power requested by the user.

The phase angle between the voltage waveform on the line 72 and the current waveform in the primary of the transformer 76 is indicative of the degree of cancelling of the reactive component of the probe impedance by tuning of the tuning inductor 36. A small or zero phase angle indicates substantially complete cancelling of the reactive component. The phase detector 50 is used to determine this phase angle by comparing the outputs of two comparators. Comparator 580 has one input coupled to line 72 and the other input coupled to a reference voltage source 582 which generally is ground. Thus each time the signal on the line 72 makes a zero crossing, the comparator 580 changes states. Another comparator 584 has one input coupled to the line 586 in the primary circuit of the step up transformer 76 and a second input coupled to a voltage reference circuit 588 which also is a ground reference voltage in the preferred embodiment. Thus each time the signal on line 586 crosses zero, the comparator 584 changes states. These changes of states on lines 590 and 592 are coupled to the phase detector 50 and carry information regarding the then existing phase angle. Since the signal on line 72 is the driving voltage and the signal on line 586 is proportional to the current passing through the probe 22 in response to the signal on the line 72, the difference in times of occurrence of the changes of states on the lines 590 and 592 can be decoded into the corresponding phase angle.

There are also provided latched status ports 600 for allowing the CPU 20 to do ground fault detection. Two of the status ports are coupled to receive the output bits from the comparators 580 and 584. Since these bits are constantly changing, the CPU 20 can tell if the probe circuit is functioning properly by reading the status ports frequently to determine if the data indicates the zero crossings are still occurring on lines 72 and 586.

There is also provided a watchdog timer circuit 602 which serves as a safeguard. The watchdog timer is constantly counting up toward a timeout number and will be continually reset by the CPU 20 by a signal on the line 606 before the timeout number is reached as long as the CPU 20 is functioning properly. If the CPU gets trapped in an endless loop or somehow fails to reset the watchdog timer 602, the timer will time out and assert a nonmaskable interrupt on line 604. The CPU 20 is slaved to the nonmaskable interrupt and will always be vectored to the service routine which serves the nonmaskable interrupt regardless of whether the CPU is in an endless loop or not. This service routine shuts down the system as a safety precaution.

Another difference between the embodiments shown in FIG. 25 and that shown in FIG. 1 is that in the embodiment of FIG. 25, the D.C. coil or flux modulating coil of the tuning inductor 36 is comprised of the two windings on either side of the center winding which is the A.C. drive winding. That is, the D.C. windings is comprised of windings 608 and 610 while the A.C. winding is the coil 612. The D.C. winding provides an inductive reactance which cancels the capacitive reactance of the probe 22 when the tuning inductor 36 is properly tuned. The D.C. windings must be such as to be able to alter the apparent inductance of the A.C. coil 612 between 0 and 30 millihenries.

In the preferred embodiment shown in FIG. 25, the user manipulated footpedal 68 is coupled to the CPU 20 through a commercially available surgical instrument called the MVS (trademark) system 610. This unit is available from Alcon Surgical Instrumentation Division in San Leandro, Calif. and is described in detail in a co-pending U.S. patent application entitled "Handpiece Drive Apparatus for Powered Surgical Scissors", Ser. No. 780,689, filed Sept. 26, 1985 which is hereby incorporated by reference. The MVS system 610 has several modes, and enables the CPU 20 when the MVS system is in the phacoemulsification mode by sending a code via the RS232 interface 70. In the phacoemulsification mode, there are two power modes available: fixed power and linear power. Which mode is entered is determined by user manipulation of the controls of the MVS system. The MVS system then sends data to the CPU 20 which controls which power mode the embodiment of the invention shown in FIG. 25 is to use. The user manipulated footpedal 68 is comprised of two switches and a potentiometer. A toggle switch is actuated between its two states when the user kicks the footpedal to the right indicating that power is to be sent to the probe. A microswitch is actuated between its two states when the user presses down on the footpedal. A linear potentiometer is also included which has its wiper mechanically coupled to the footpedal so that when the footpedal is pressed down, the wiper is moved. The MVS system 610 has an analog-to-digital converter which is coupled to the potentiometer which converts the setting of the potentiometer to a digital value indicative of the desired level of power requested by the user. The MVS system is also coupled to the toggle switch and to the microswitch through I/O ports (not shown) so that the MVS system can read the states of these two switches. The MVS system converts the states of the two switches and the setting of the potentiometer to digital data or code words which are sent to the CpU 20 via the RS232 interface. In the preferred embodiment, the MVS system after enabling the CPU 20 in the Phacoemulsification mode, generates an interrupt to the CPU 20 when the toggle switch indicates the footpedal is kicked right and when the microswitch indicates the footpedal has been pushed down. The CPU 20 is then vectored to a power control service routine which reads the data as to the toggle switch position, the microswitch position and the potentiometer setting. This service routine is described next.

Figures 29A, 29B:
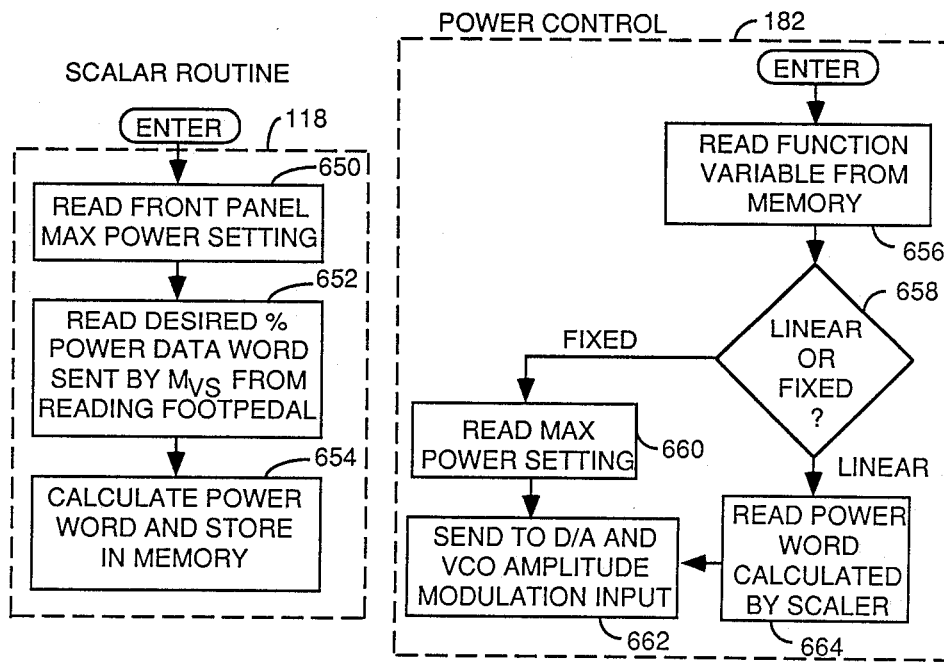
FIGS. 29A and 29B are flow charts of the details of the power control step 182 in FIG. 6C and a scalar routine which is performed as part of step 118 in FIG. 5, respectively.

Referring to FIG. 29A, there is shown the details of the power control steps to control the power sent to the probe 22 during phacoemulcification operations. The embodiment of the invention shown in FIG. 25 can operate in a fixed power mode or a linear power mode. In the fixed power mode, the maximum power set by the user in the front panel switch 64 is sent to the probe 22 when the user depresses the footpedal any amount in the phacoemulsification mode of the MVS system. Of course in alternative embodiments, the MVS system 610 may be eliminated as the footpedal interface. and the footpedal 68 may be directly coupled to the CPU through appropriate, conventional interface circuitry. In the linear power control mode a percentage of the maximum power set in the maximum power switch 64 is sent to the probe 22 where the percentage depends upon the position of the footpedal. The power control is linear such that a 10% increase in the displacement of the footpedal results in a 10% increase in power dissipation in the probe.

There is a scaler routine which is performed as part of step 118 shown in FIG. 5 which constantly performs the scaling calculation for the linear mode each time step 118 is performed. The steps of this calculation are shown in FIG. 29B. The first step is symbolized by block 650 which reads the front panel maximum power setting set by the user on switch 64. Next, step 652 reads the desired percentage of power data which is derived by the MVS system from reading the position of the potentiomeer in the footpedal. The MVS system writes this data to the CPU 20 via the RS232 communications interface 70. The desired percentage of power is then multiplied by the maximum power setting to derive a power word which is stored in memory as symbolized by step 654. Processing then continues with the other operations of step 118 and from there to step 120 in FIG. B.

The steps to the right in FIG. 29A are the details of the power control step 182 in FIG. 6C. The flow charts of FIGS. 5 and 6A through 6C are used in the embodiment of FIG. 25, but the flow charts of FIGS. 7 through 17 are replaced by the frequency tuning and phase angle adjusting routines of FIGS. 27 and 28 respectively. The first substep in the power control step 118 is symbolized by block 656 which reads the function variable from memory. This function variable is stored in memory by the keyboard scan routine which reads the switches on the front panel to determine whether the user wishes to operate in the linear or the fixed power modes. Substep 658 determines what the function variable states regarding the mode, and vectors processing to substep 660 if the mode is fixed. Substep 660 reads the maximum power setting either from the front panel switches or from the memory location in which this data is stored by the keyboard scan routine. Next, this maximum power setting is sent as a digital word to the D/A converter 560 by the CPU 20 for conversion to an analog signal which controls the amplitude of the signal put out by the VCO 56 as symbolized by substep 662.

If substep 658 determines that the linear power control mode is selected, a step 664 is performed which reads the power word calculated by the scaler routine in step 118 and sends this power control data word to the D/A converter 560 and the VCO amplitude modulation control input to set the desired amplitude of the driving signal.

Figure 26:
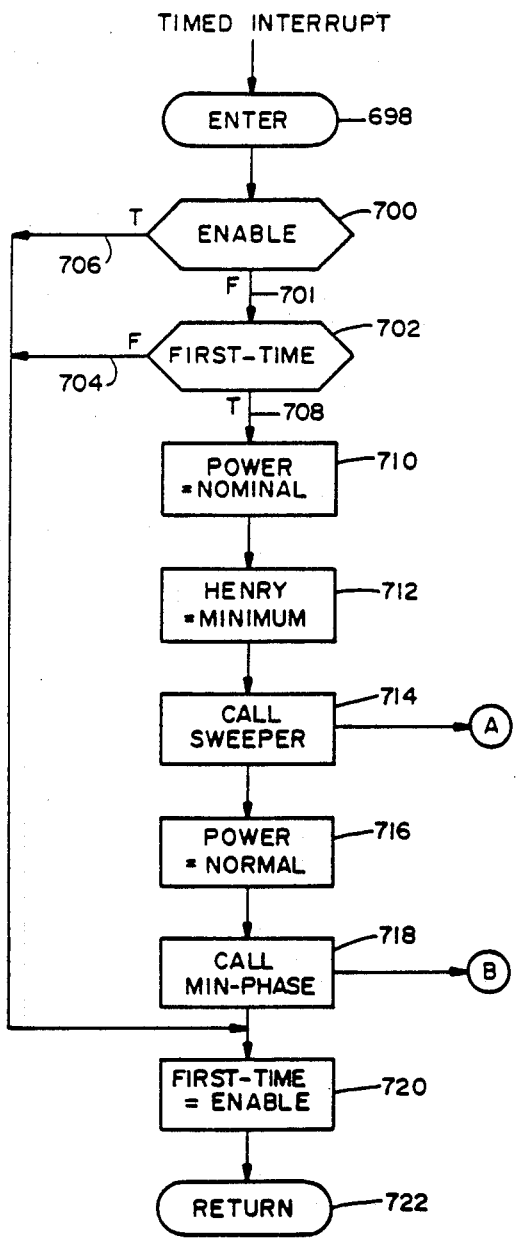
FIG. 26 is a flow chart of the software of the main loop of the control program of the invention.

Referring to FIG. 26 there is shown a flow diagram of the calibration cycle of the control program of the preferred embodiment of the invention. The calibration cycle of the program is periodically run but the core steps that tune the frequency and minimize the phase angle are run only one time each time the user lets up on the footpedal thereby indicating that the user does not want power dissipated in the probe. Basically the control software that controls the operation of the system of FIG. 25 is set up as a series of interrupt service routines that occur periodically. The calibration cycle routine of FIG. 26 can be one of these timed routines that performs the frequency sweep and phase angle minimization only once each time the user lets up the footpedal and bypasses these steps when the user is applying power to the probe. In alternative embodiments, other software architectures may be used. It is important however in obtaining maximum performance that whatever software architecture is chosen find the probe resonant frequency and match the VCO driver frequency to the resonant frequency of the probe and it is important that once this is done, that the tuning inductor be tuned to minimize the phase angle as much as possible. Whatever software architecture that performs these functions and provides linear power control will suffice for purposes of practicing the invention, and the particular software architecture that is described here is not critical to the invention.

The calibration cycle essentially determines whether or not it is time to do a frequency sweep and phase angle minimization. To that end, the calibration cycle of FIG. 26 starts out with an enter step 698. This step symbolizes the timed interrupt that periodically occurs and is self generated by a timer in the CPU 20. Each time this interrupt occurs, processing jumps to step 698, and the calibration cycle is performed. The first step in the calibration cycle is the enable step 700 which checks an enable flag in RAM which indicates whether the user has taken his or her foot off the footpedal indicating the user does not wish to send power to the probe. Step 700 represents the step of checking the status flag in RAM that indicates this status and branching to the appropriate next step depending upon the condition of the status flag. A status routine (not shown) periodically reads the control codes arriving from the MVS system 610 regarding the positions of the switches in the footpedal and updates the status flags. The control codes regarding the toggle switch and the microswitch status in the footpedal are used to set the power status flag read by step 700.

Assuming that the flag status checked in step 700 indicates that the user has lifted his foot from the footpedal, processing proceeds to a step 702 to determine if this is the first time since entering at step 698 that the enable step 700 has vectored processing along the path 701. The reason for this is to prevent the calibration routine of the steps following step 702 from being performed more than once each time the user takes his foot off the footpedal. If the steps following step 702 have already been performed once since the routine of FIG. 26 was entered then processing is vectored along path 704. Likewise, if the routine of FIG. 26 is entered at a time when the user is applying power to the probe, then the test of step 700 vectors processing along the path 706. Paths 704 and 706 bypass the calibration step following step 702.

Assuming that path 708 is followed out of step 702, a step 710 is performed. This step sets the power level to the probe to a nominal level by writing an appropriate digital word to the D/A converter 560 in FIG. 25. Next a step 712 is performed to set the inductance of the tuning inductor 36 to a minimum value. This is done by writing a digital word to the D/A converter 40 which sets the current flow through the D.C. bias coils 610 and 608 to a maximum level.

Next, a step 714 is performed to call the sweeper routine to be described below. The purpose of this routine is to sweep the frequency of the VCO 56 through an entire range of driving frequencies which will include the resonant frequency of any probe 22 attached to the system which is intended for phacoemulsification operations. At each frequency, the driving current is read and compared to the highest driving current previously recorded to determine if a new highest driving current has been found. The frequency at which the highest driving current flow is found is the resonant frequency of the probe.

After the sweeper routine finds the resonant frequency of the probe, the frequency to the VCO is set at this frequency via a write operation to the D/A converter 170, and processing proceeds to step 716.

Step 716 sets the power level to the probe back to the normal level which existed before the routine of FIG. 26 was entered.

Following step 716, a step 718 is performed which serves to minimize the phase angle at the new driving frequency. This routine will be described more below. Finally, a step 720 is performed which sets the FIRST_TIME flag checked in step 702 to indicate that the calibration routine has been performed once since the user first removed power to the probe. Finally, processing returns from the interrupt service routine of FIG. 26 to the point in the program where processing halted when the interrupt that vectored processing to step 698 occurred. This is symbolized by step 722. Processing then proceeds from that point.

Figure 27:
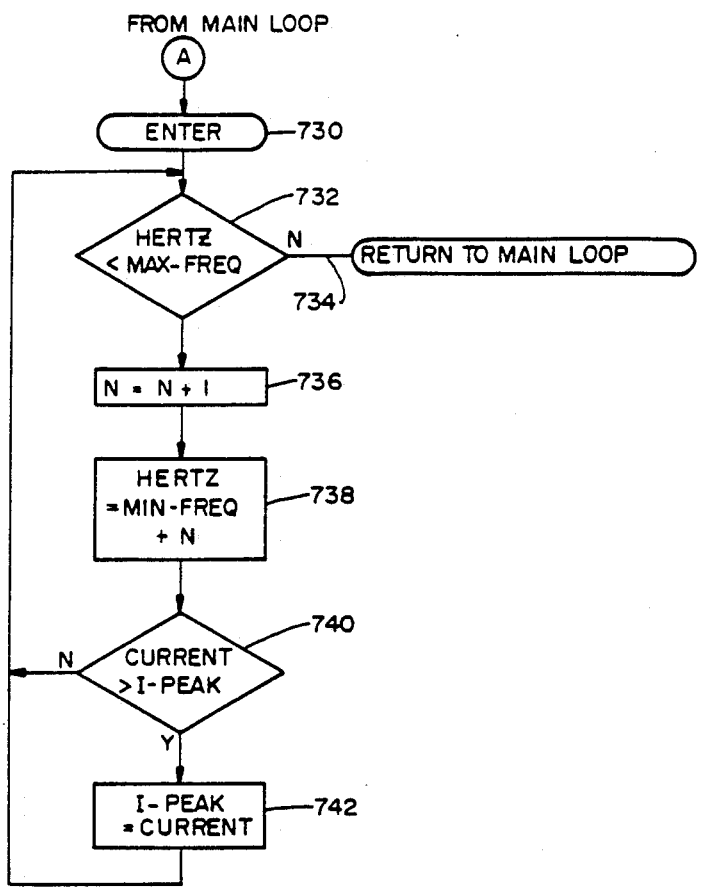
FIG. 27 is a flow chart of the frequency sweeper subroutine called upon by the main loop to determine the drive frequency which maximizes the drive current for the probe 22.

Referring to FIG. 27, the details of the sweeper routine are given. Step 730 symbolizes the call of this subroutine from step 714 in FIG. 26. Next, a test symbolized by step 732 is performed. The purpose of this test is to determine if the current operating frequency of the VCO is at or above the fixed, high frequency end of the band of frequencies through which the VCO frequency is swept to find the resonant frequency of the probe. If the frequency has been increased to the high frequency boundary or above, processing is vectored along path 734 which symbolizes the return to the routine of FIG. 26, step 716. If the frequency has not yet reached the high end of the frequency band, processing proceeds to step 736 which increments the incrementation variable N by 1 step. When the routine of FIG. 27 was entered step 730 initialized N to zero.

Next, a step 736 is performed. This step symbolizes the step of incrementing the VCO frequency to the next higher frequency step. The first time the loop of FIG. 27 is performed N is zero and step 738 sets the VCO frequency to the MIN_FREQ value which is the frequency boundary at the low end of the range of frequencies through which the VCO frequency is swept. Each time the loop is performed, N is incremented by one, and the frequency of the VCO is set one step higher until the test of step 732 returns processing to the routine of FIG. 26. Step 738 also symbolizes the process of writing the digital word representing the new frequency out to the D/A converter 170 in FIG. 25 to set the VCO frequency to the new frequency.

Next, a step 740 is performed to read the new resulting drive current through the probe and compare it to the current value of the variable I_PEAK in which the maximum drive current so far recorded is stored. The first substep in this process is the addressing and reading of the digital word at the channel 2 output of the A/D converter 54 in FIG. 25. This digital word represents the magnitude of the primary current in the transformer 76 as sensed by the current sensor 550 and is proportional to the actual drive current flowing through the probe 22. Then, the value stored in the I PEAK variable is compared against the current data just obtained to see is the drive current is now greater than the previous peak drive current. If it is, the I_PEAK variable contents are updated with the value of the drive current at the then existing drive frequency and the value of this drive frequency is recorded as associated with the drive current just written to I PEAK. This process is symbolized by step 742. Processing is then vectored to step 732 to start the loop again.

Figure 28:
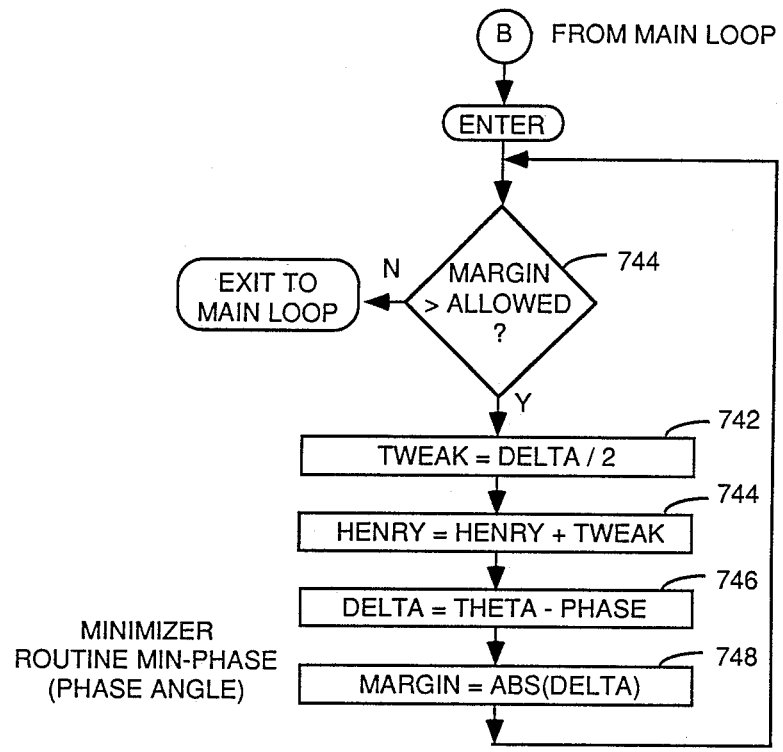
FIG. 28 is a flow chart of the phase angle minimization subroutine called upon by the main loop to tune the tuning inductor to change the inductive reactance of the source impedance to match the capacitive reactance of the probe as close as possible.

Referring to FIG. 28, the details of the phase angle minimizer routine are given. The first step in this routine when it is called from step 718 in FIG. 26 is to determine if the current phase angle is within a band of allowed phase angles centered around the desired phase angle. This test is symbolized by step 744. The reason this step is performed is to prevent the loop of FIG. 28 from being performed an infinite number of times since a successive approximation technique is used where adjustments of only half the error margin are made. The step 744 compares the contents of variable MARGIN to a constant called ALLOWED which is the maximum error margin which is allowed. If MARGIN is greater than ALLOWED, step 742 is performed which adjusts the contents to a variable TWEAK which is the amount by which the current in the D.C. bias coils 608 and 610 is to be changed to start the process of tuning away the phase angle to the minimum possible angle. TWEAK is adjusted by step 742 by an amount equal to DELTA/2 where DELTA is the signed difference between the desired phase angle (expressed in terms of the current though the D.C. bias coils) and the actual phase angle. The actual phase angle is determined by the CPU 20 by reading the channel 1 output of the A/D converter 54 in FIG. 25 to obtain the results calculated by the phase detector 50 and the summer and integrator 52. The desired phase angle can be any constant, but is usually zero.

Next, a step 744 is performed which adjusts the current level in the D.C. bias coils 608 and 610 in FIG. 25 to a new level of current in an attempt to minimize the phase angle. In step 744, a variable HENRY. Which represents the current value of current flowing in the D.C. bias coils 608 and 610 expressed in terms of the digital value currently written to the D/A converter 40, is changed by the value of TWEAK.

Next, a step 746 is performed to test the new phase angle which results from the change in HENRY and the resultant change in the current level flowing in the D.C.

bias coils. Step 746 computes the value of the variable DELTA by subtracting from the desired phase angle, TMETA, the value of the current phase as determined by reading the channel 1 output from the A/D converter 54 as represented by the variable PHASE. Next, a step 748 is performed which computes the value of the variable MARGIN by taking the absolute value of the variable DELTA.

Finally, processing is returned to the test of 744. When the test of step 744 indicates that MARGIN is less than the value of ALLOWED, processing returns to the routine of FIG. 26, step 720.

Although the intention has been described in terms of the preferred and alternative embodiments disclosed herein, those skilled in the art will appreciate many modifications which may be made without departing from the true spirit and scope of the invention. All such embodiments are intended to be included within the scope of the claims appended hereto.

What is claimed is:

1. A method of driving an ultrasonically driven probe having an electronically tunable reactance coupled to said probe comprising the steps of:
   generating a driving signal having a frequency within a band of frequencies encompassing the mechanical resonance frequency of said probe;
   measuring the relative amount of drive current to said probe resulting from said drive signal at said frequency;
   comparing said drive current to a variable which is updated to store the value of the highest drive current at any other drive frequency in said band of frequencies;
   if said drive current is higher than said variable, updating the value of said variable with the value of said drive current and recording the frequency of said driving signal that resulted in said new highest drive current;
   adjusting the frequency of said driving signal to a new frequency in the band of frequencies and repeating the above steps for the new frequency; and
   repeating the step next above until all frequencies in the band of frequencies have been generated and the resulting drive currents measured;
   setting the frequency of said driving signal to the frequency in said band of frequencies which resulted in the highest drive current;
   measuring the phase angle between said drive current and the driving signal voltage at said frequency which resulted in said highest drive current and comparing said phase angle to a selected margin defining a range of acceptable phase angles;
   if said phase angle is outside the range of acceptable phase angles, electronically tuning said reactance to a new value and measuring said phase angle again and comparing said phase angle to said acceptable range of phase angles;
   repeating the step next above until said phase angle is within said acceptable range.

2. An apparatus for ultrasonically driving a probe having a mechanical resonant frequency, comprising:
   first means for generating a driving signal for said probe and having an input for receiving a first control signal to control the frequency of said driving signal and for coupling said driving signal to said probe so as to cause load current to flow therein;
   second means coupled to said first means to determine the mechanical resonant frequency of said probe by generating said first control signal so as to incrementally after the frequency of said driving signal throughout a range of frequencies encompassing the mechanical resonance frequency of said probe, and measuring the load current through said probe resulting from said driving signal at each frequency in said range of frequencies and for recording the frequency at which said load current is a maximum and, thereafter, to generate said first control signal so as to tune said first means to generate said driving signal at the frequency which caused said load current to be a maximum;
   a tuning inductor for coupling said drive signal to said probe such that said driving signal passes through said tuning inductor, and having an input for receiving a second control signal which controls the amount of inductance of said tuning inductor;
   means coupled to said tuning inductor for generating said second control signal so as to cause the inductance of said tuning inductor to be at a minimum during the interval when the frequency of said driving signal to being incrementally altered throughout said range of frequencies, and, after said frequency of said driving signal has been set at the frequency which caused said maximum load current, for measuring the phase angle between the voltage of said driving signal and the resultant load current and for generating said second control signal at a level which alters the inductance of said tuning inductor in such a way as to alter said phase angle to be within a predetermined range.

3. An apparatus as defined in claim 2 wherein said first means also has an input for receiving a third control signal which controls the amplitude of the driving signal generating by said first means, and wherein said apparatus further comprises means coupled to said input of said first means to receive said third control signal for receiving a signal from an external source indicating the desired amount of power to be dissipated in said probe and for generating said third control signal so as to linearly control the amplitude of said driving signal in accordance with the signal from said external source, and wherein said second means includes a step up transformer coupled to said driving signal for said probe in such a manner as to sense the load current flowing through said probe and to generate a voltage which is proportional to and in phase with said load current for use in measuring said probe load current.

4. An apparatus for driving an ultrasonic probe with linear power control comprising:
   first means for generating a driving signal for said probe and having an input for receiving a first control signal to control the frequency of said driving signal;
   second means coupled to said first means to occasionally finding the mechanical resonant frequency of said probe under then existing conditions by finding the frequency for said driving signal which causes load current through said probe caused by said driving signal to be maximized and for generating said first control signal to tune said first means so as to generate a driving signal at the mechanical resonant frequency of said probe;
   a tuning inductor including an inductor in series with said probe for coupling said drive signal to said probe and having an input for receiving a second control signal which controls the amount of inductance of said tuning inductor;

third means coupled to said tuning inductor for minimizing the inductance of said tuning inductor at first predetermined times and for, at second predetermined times, determining the actual phase angle between the driving signal voltage for said probe and the resulting load current and for determining the difference between said actual phase angle and a desired phase angle and for generating said second control signal to tune said tuning inductor to alter said phase angle so as to be within a selected range;

a foot-operated power control transducer;

and wherein said first means also has an input for receiving a third control signal which controls the amplitude of the driving signal generated by said first means; and further comprising means coupled to said first means for determining the desired amount of power to by dissipated in said probe by reading said foot-operated power control transducer and for generating said third control signal so as to control the amplitude of said driving signal linearly in accordance with the setting of said foot-operated power control transducer;

and further comprising ground fault detection means coupled to said driving signal and to said first means for determining whether said first means and said probe are operating and for generating a control signal which causes said first means to stop generating said driving signal in predetermined circumstances.

5. An apparatus for driving a phacoemulsification probe containing piezoelectric crystal excitation element comprising:

a footpedal power control;

a maximum power control;

a variable inductor having an inductance value which can be electronically altered;

first means for generating variable frequency, variable amplitude alternating current driving signal for said crystal and having a first control input for receiving a first control signal which controls the frequency of said driving signal and having a second control input for receiving a second control signal which controls the amplitude of said driving signal;

second means coupled to said first means for determining the desired power level by reading the position of said footpedal indicating the desired percentage of maximum power and reading the position of said maximum power control to determine the maximum power and calculating the actual power desired using said maximum power and said percentage of maximum power and for generating said second control signal so as to be a linear function of the footpedal position;

third means coupled to said first means for generating said first control signal so as to sweep said frequency of said driving signal through a range of frequencies and for measuring the load current through said probe at various ones of said frequencies to determine the frequency at which said load current is a maximum and for generating said first control signal such that said driving signal has the frequency which caused the maximum load current to flow;

means for determining the phase difference between the voltage waveform for the voltage across said probe and current waveforms for the current through said probe resulting from said voltage waveform of the amplified driving signal and for generating an error signal indicating the value of said phase difference;

means for receiving said error signal and for electronically changing the inductance value of said variable inductor to alter said phase angle to within a range of acceptable values.

6. The apparatus of claim 5 wherein said third means includes a voltage step up current sense transformer coupled to sense the level of drive current through said probe.

7. The apparatus of claim 5 further comprising ground fault detection means coupled to said driving signal for causing said first means to stop generating said driving signal under predetermined conditions including the lack of current flow through said crystal and further comprises timer means for causing said first means to stop generating said driving signal in the event of a timeout occurring, said timer means including means for preventing said timeout unless a predetermined event occurs.

* * * * *

UNITED STATES PATENT AND TRADEMARK OFFICE
CERTIFICATE OF CORRECTION

PATENT NO.   : 4,954,960
DATED        : 09/04/90
INVENTOR(S)  : T. Lo, et al.

It is certified that error appears in the above-identified patent and that said Letters Patent is hereby corrected as shown below:

Column 1, line 28, delete "." and insert --,--

Column 4, line 33, delete "Width" and insert --width--

Column 5, line 26, delete "tuning" and insert --turning--

Column 6, line 11, delete ". Power" and insert --, power --

Column 13, lines 17, 45, delete "eguivalent" and insert --equivalent"

Column 14, line 49, delete "processing" and insert --Processing--

Column 22, line 7, delete "of" and insert --for--

Column 25, line 29, delete "shematic" and insert --schematic--

Column 26, line 4 delete "retriggerabIe" and insert "retriggerable--

Column 31, line 24, delete "t he" and insert --the--

UNITED STATES PATENT AND TRADEMARK OFFICE
CERTIFICATE OF CORRECTION

PATENT NO. : 4,954,960

DATED : September 4, 1990

INVENTOR(S) : T. Lo, et. al.

It is certified that error appears in the above-identified patent and that said Letters Patent is hereby corrected as shown below:

Column 32, line 39, insert after "1985" -- now U.S. Patent 4,768,506 issud Sept. 6, 1988--.

Signed and Sealed this

Twenty-third Day of February, 1993

Attest:

STEPHEN G. KUNIN

Attesting Officer

Acting Commissioner of Patents and Trademarks